United States Patent [19]
Daggett et al.

[11] Patent Number: 5,912,122
[45] Date of Patent: Jun. 15, 1999

[54] NUCLEIC ACIDS ENCODING AND METHOD FOR DETECTING NUCLEIC ACID ENCODING HUMAN METABOTROPIC GLUTAMATE RECEPTOR SUBTYPE MGLUR6

[75] Inventors: Lorrie P. Daggett; Chin-Chun Lu, both of San Diego, Calif.

[73] Assignee: Sibia Neurosciences, Inc., La Jolla, Calif.

[21] Appl. No.: 08/407,875

[22] Filed: Mar. 20, 1995

Related U.S. Application Data

[63] Continuation-in-part of application No. 08/072,574, Jun. 4, 1993, Pat. No. 5,521,297.
[51] Int. Cl.$^6$ .............................. C12N 15/85; C07H 21/04
[52] U.S. Cl. ........................... 435/6; 536/23.5; 536/24.31; 435/325
[58] Field of Search ................. 536/23.5, 24.31; 435/320.1, 240.2, 6, 325

[56] References Cited

U.S. PATENT DOCUMENTS

| | | | |
|---|---|---|---|
| 4,837,148 | 6/1989 | Cregg | 530/350 |
| 4,855,231 | 8/1989 | Stroman et al. | 435/6 |
| 4,882,279 | 11/1989 | Cregg | 530/350 |
| 4,929,555 | 5/1990 | Cregg et al. | 435/6 |
| 5,024,939 | 6/1991 | Gorman | 530/350 |
| 5,385,831 | 1/1995 | Mulvihill et al. | 435/6 |

FOREIGN PATENT DOCUMENTS

| | | |
|---|---|---|
| 0569240 | 10/1993 | European Pat. Off. . |
| 0 569 240 A1 | 11/1993 | European Pat. Off. . |
| WO 89/09834 | 10/1989 | WIPO . |
| WO 91/13077 | 9/1991 | WIPO . |
| WO 92/02639 | 2/1992 | WIPO . |
| WO 93/04083 | 3/1993 | WIPO . |
| WO 93/13423 | 7/1993 | WIPO . |
| WO 94/29449 | 12/1994 | WIPO . |
| WO 95/08627 | 3/1995 | WIPO . |
| WO 95/18154 | 7/1995 | WIPO . |
| WO 95/22609 | 8/1995 | WIPO . |
| WO 96/06167 | 2/1996 | WIPO . |

OTHER PUBLICATIONS

Makoff et al., "Molecular characterization and localization of human metabotropic glutamate receptor type 4" *Molecular Brain Research* 37:239–248 (1996).

Abe et al., "Molecular Characterization of a Novel Metabotropic Glutamate Receptor mGluR5 Coupled to Inositol Phosphate/$Ca^{2+}$ Signal Transduction" *J. Biol. Chem.* 267:13361–13368 (1992).

Bahouth et al., "Immunological approaches for probing receptor structure and function" *Trends Pharmacol. Sci.* 12:338–343 (1991).

Biel et al., "Another member of the cyclic nucleotide–grated channel family, expressed in testis, kidney, and heart" *Proc. Natl. Acad. Sci. USA* 91:3505–3509 (1994).

Brabet et al., "Phenylglycine Derivatives Discriminate Between mGluR1– and mGluR5–mediated Responses" *Neuropharmacol.* 34:895–903 (1995).

Marion M. Bradford, "A Rapid and Sensitive Method for the Quantitation of Microgram Quantities of Protein Utilizing the Principle of Protein–Dye Binding" *Anal Biochem.* 72:248–254 (1976).

Bradley et al., "Heteromeric olfactory cyclic nucleotide–grated channels: A subunit that confers increased sensitivity to cAMP" *Proc. Natl. Acad. Sci. USA* 91:8890–8894 (1994).

Bruno et al., "Activation of Metabotropic Glutamate Receptors Coupled to Inositol Phospholipid Hydrolysis Amplifies NMDA–induced Neuronal Degeneration in Cultured Cortical Cells" *Neuropharmacol.* 34:1089–1098 (1995).

Buisson and Choi, "The Inhibitory mGluR Agonist, s–4–carboxy–3–hydroxy–phenylglycine Selectively Attenuates NMDA Neurotoxicity and Oxygen—Glucose Deprivation–induced Neuronal Death" *Neuropharmacol.* 34:1081–1087 (1995).

F. Conquet, "Inactivation In Vivo of Metabotropic Glutamate Receptor 1 by Specific Chromosomal Insertion of Reporter Gene 1acZ" *Neuropharmacol.* 34:865–870 (1995).

Daggett et al., "Molecular and Functional Characterization of Recombinant Human Metabotropic Glutamate Receptor Subtype 5" *Neuropharmacol.* 34:871–886 (1995).

Dani and Mayer, "Structure and function of glutamate and nicotinic acetylcholine receptors" *Curr. Opp. Neurobiol.* 5:310–317 (1995).

Nathan Dascal, "The Use of *Xenopus Oocytes* For The Study of Ion Channels" *Crit. Rev. Biochem.* 22:317–387 (1987).

David T. Denhardt, "A Membrane–Filter Technique For The Detection Of Complementary DNA" *Biochem. Biophys. Res. Commun.* 23:641–646 (1966).

Dhallan et al., "Primary structure and functional expression of a cyclic nucleotide–activated channel from olfactory neurons" *Nature* 347:184–187 (1990).

Felder, et al., "A Transfected m1 Muscarinic Acetylcholine Receptor Stimulates Adenylate Cyclase via Phosphatidylinositol Hydrolysis" *J. Bio. Chem.* 264:20356–20362 (1989).

(List continued on next page.)

*Primary Examiner*—Lisa B. Arthur
*Attorney, Agent, or Firm*—Stephen E. Reiter; Gray Cary Ware & Freidenrich LLP

[57] ABSTRACT

In accordance with the present invention, there are provided nucleic acids encoding human metabotropic glutamate receptor subtype mGluR6, and the proteins encoded thereby. In addition to being useful for the production of metabotropic glutamate receptor subtype mGluR6, nucleic acids of the invention are also useful as probes, thus enabling those skilled in the art, without undue experimentation, to identify and isolate related human receptor subunits. In addition to disclosing a novel metabotropic glutamate receptor subtype, mGluR6, the present invention also comprises methods for using the invention receptor subtype to identify and characterize compounds which affect the function of such receptor subtype, e.g., agonists, antagonists, and modulators of glutamate receptor function.

12 Claims, 1 Drawing Sheet

OTHER PUBLICATIONS

Fisher and Aronson, Jr., "Characterization of the cDNA and Genomic Sequence of a G Protein γ Subunit (γ₅)" *Mol. Cell Bio.* 12:1585–1591 (1992).

Gautam et al., "G protein diversity is increased by associations with a variety of γ subumits" *Proc. Natl. Acad. Sci. USA* 87:7973–7977 (1990).

Gautam et al., "A G Protein Gamma Subunit Shares Homology with ras Proteins" *Science* 244:971–974 (1989).

Grynkiewicz et al., "A New Generation of $Ca^{2+}$ Indicators with Greatly Improved Fluorescence Properties" *J. Biol. Chem.* 260:3440–3450 (1985).

Gundersen et al., "Glutamate and kainate receptors induced by rat brain messenger RNA in *Xenopus oocytes*" *Proc. R. Soc. Lond.* 221:127–143 (1984).

Hammer et al., "Production of transgenic rabbits, sheep and pigs by microinjection" *Nature* 315:680–683 (1985).

Hurley et al., "Isolation and characterization of a cDNA clone for the γ subunit of bovine retinal transducin" *Proc. Natl. Acad. Sci. USA* 81:6948–6952 (1984).

Ito et al., "Characterization of Prostaglandin $E_2$–Induced $Ca^{2+}$ Mobilization in Single Bovine Adrenal Chromaffin Cells by Digital Image Microscopy" *J. Neurochem.* 56:531–540 (1991).

Kaupp et al., "Primary structure and functional expression from complementary DNA of the rod photoreceptor cyclic GMP–gated channel" *Nature* 342:762–766 (1989).

Kingston et al., "Pharmacological Analysis of 4–Carboxyphenylglycine Derivatives: Comparison of Effects on mGluR1α and mGluR5a Subtypes" *Neuropharmacol.* 34:887–894 (1995).

Kleuss et al., "Selectivity in Signal Transduction Determined by γ Subunits of Heterotrimeric G Proteins" *Science* 259:832–834 (1993).

Knöpfel et al., "Pharmacological Characterization of MCCG and MAP4 at the mGluR1b, mGluR2 and mGluR4a Human Metabotropic Glutamate Receptor Subtypes" *Neuropharmacol.* 34:1099–1102 (1995).

Marilyn Kozak, "Structural Features in Eukaryotic mRNAs That Modulate the Initiation of Translation" *J. Biol. Chem.* 226:19867–19870 (1991).

Krieg and Melton, "Functional messenger RNAs are produced by SP6 in vitro transcription of cloned cDNAs" *Nucleic Acids Res.* 12:7057–7070 (1984).

Kyte and Doolittle, "A Simple Method for Displaying Hydropathic Character of a Protein" *J. Mol. Biol.* 157:105–132 (1982).

Liebman and Tavormina Evanczuk, "Real Time Assay of Rod Disk Membrane cGMP Phosphodiesterase and Its Controller Enzymes" *Meth. Enzymol.* 81:532–542 ((1994).

Liman and Buck, "A Second Subunit of the Olfactory Cyclic Nucleotide—Gated Channel Confers High Sensitivity of cAMP" *Neuron* 13:611–621 (1994).

Linder and Gilman, "G Proteins, Tucked into the internal surface of the cell's outer membrane, these versatile molecules coordinate cellular responses to a multitude of signals that impinge from without" *Sci. Am.* 267:56–65 (1992).

Masu et al., "Specific Deficit of the ON Response in Visual Transmission by Targeted Disruption of the mGluR6 Gene" *Cell* 80:757–765 (1995).

J. H. Miller, "Assay of β–Galactosidase" *Book–Exp in Mol. Genetics* Experiment 48:352–355 (1972).

Monaghan et al., "The Excitatory Amino Acid Receptors: Their Classes, Pharmacology, and Distinct Properties in the Function of the Central Nervous System" *Annu. Rev. Pharmacol. Toxicol.* 29:365–402 (1989).

Nakajima et al., "Direct Linkage of Three Tachykinin Receptors to Stimulation of Both Phosphatidylinositol Hydrolysis and Cyclic AMP Cascades in Transfected Chinese Hamster Ovary Cells" *J. Biol. Chem.* 267:2437–2442 (1992).

Nakajima et al., "Molecular Characterization of a Retinal Metabotropic Glutamate Receptor mGluR6 with a High Agonist Selectivity for L–2–Amino–4–phosphonobutyrate" *J. Biol. Chem.* 268:11868–11873 (1993).

Shigetada Nakanishi, "Metabotropic Glutamate Receptors: Synaptic Transmission, Modulation, and Plasticity" *Neuron* 13:1031–1037 (1994).

Nicoletti et al., "The Activation of Inositol Phospholipid Metabolism as a Signal–Transducing System for Excitatory Amino Acids in Primary Cultures of Cerebellar Granule Cells" *J. Neuroscience* 6:1905–1911 (1986).

Pin and Bockaert, "Get receptive to metabotropic glutamate receptors" *Curr. Opp. Neurobio.* 5:342–349 (1995).

Pin and Duvoisin, "Neurotransmitter receptors I, The Metabotropic Glutamate Receptors: Structure and Functions" *Neuropharmacol.* 34:1–26 (1994).

Schoepp et al., "Selective Inhibition of Forskolin–stimulated Cyclic AMP Formation in Rat Hippocampus by a Novel mGluR Agonist, 2R, 4R–4–aminopyrrolidine–2, 4–dicarboxylate" *Neuropharmacol.* 34:843–850 (1995).

Schoepp and True, "1S,3R–ACPD–sensitive (metabotropic) [$^3$H]glutamate receptor binding in membranes" *Neuroscience Lett.* 145:100–104 (1992).

Simon et al., "Diversity of G Proteins in Signal Transduction" *Science* 252:802–808 (1991).

Sladeczek et al., "Glutamate stimulates inositol phosphate formation in striatal neurones" *Nature* 317:717–719 (1985).

Steiner et al., "Radioimmunoassay for Cyclic Nucleotides" *J. Biol. Chem.* 247:1106–1113 (1972).

Stillman and Gluzman, "Replication and Supercoiling of Simian Virus 40 DNA in Cell Extracts from Human Cells" *Mol. Cell. Biol.* 5:2051–2060 (1985).

Walter Stühmer, "Electrophysiological Recording from *Xenopus Oocytes*" *Meth. Enzymol.* 207:319–339 (1992).

Sugiyama et al., "A new type of glutamate receptor linked to inositol phospholipid metabolism" *Nature* 325:531–533 (1987).

Tamir et al., "G–Protein βγ Forms: Identity of β and Diversity of γ Subunits" *Biochem.* 30:3929–3936 (1991).

Tanabe et al., "A Family of Metabotropic Glutamate Receptors" *Neuron* 8:169–179 (1992).

Urlaub et al., "Effect of Gamma Rays at the Dihydrofolate Reductase Locus: Deletions and Inversions" *Somatic Cell Mol. Genetics* 12:555–566 (1986).

Waechter and Baserga, "Effect of methylation on expression of microinjected genes" *Prac. Natl. Acad. Sci. USA* 79:1106–1110 (1982).

Wickman and Clapham, "G–protein regulation of ion channels" *Curr. Opp. Neurobiol.* 5:278–285 (1995).

Wigler et al., "DNA–mediated transfer of the adenine phosphoribosyltransferase locus into mammalian cell" *Proc. Natl. Acad. Sci. USA* 76:1373–1376 (1979).

Flor et al. Neuropharmacology (1995) 34(2):149–155.

Flor et al. Soc. Neurosci. Abstr. 20:468 (1994).

Minakami et al. Biochem Biophys. Res. Com. (1994) 199(3): 1136–1143.

NUCLEIC ACIDS ENCODING AND METHOD FOR DETECTING NUCLEIC ACID ENCODING HUMAN METABOTROPIC GLUTAMATE RECEPTOR SUBTYPE MGLUR6

The present application is a continuation-in-part of U.S. Ser. No. 08/072,574, filed Jun. 4, 1993, now U.S. Pat. No. 5,521,297.

The present invention relates to nucleic acids and receptor proteins encoded thereby. Invention nucleic acids encode novel human metabotropic glutamate receptor subtypes. The invention also relates to methods for making such receptor subtypes and for using the receptor proteins in assays designed to identify and characterize compounds which affect the function of such receptors, e.g., agonists, antagonists, and allosteric modulators of human metabotropic glutamate receptors.

BACKGROUND OF THE INVENTION

The amino acid L-glutamate is a major excitatory neurotransmitter in the mammalian central nervous system Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are NMDA (N-methyl-D-aspartate) receptors and kainate/AMPA (α-amino-3-hydroxy-5-methyl-4-isoxazole propionate, formerly called the quisqualic acid or QUIS receptor), receptors. While the metabotropic receptors bind to some of the same ligands that bind to ionotropic glutamate receptors, the metabotropic receptors alter synaptic physiology via GTP-binding proteins and second messengers such as adenylate cyclase, cyclic AMP, phosphodiesterases, cyclic GMP, diacylglycerol, inositol 1,4,5-triphosphate protein kinases and calcium [see, for example, Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987); and Pin. J.-P. and Duvoisin, R. Neuropharmacology 34:1–26 (1994)].

The electrophysiological and pharmacological properties of metabotropic glutamate receptors have been studied using animal tissues and cell lines as a source of receptors, as well as non-human recombinant receptors. These studies have indicated that multiple subtypes of metabotropic glutamate receptors exist. Because of the potential physiological and pathological significance of metabotropic glutamate receptors, it is imperative (particularly for drug screening assays) to have available human sequences (i.e., DNA, RNA, proteins) which encode representative members of each of the various metabotropic glutamate receptor subtypes. The availability of such human sequences is critical to the development of human therapeutics that specifically target individual metabotropic receptor subtypes and will also enable the investigation of receptor distribution in humans, the correlation of specific receptor modification with the occurrence of various disease states, etc.

BRIEF DESCRIPTION OF THE INVENTION

The present invention discloses novel nucleic acids encoding human metabotropic glutamate receptor protein subtype mGluR6, and the proteins encoded thereby. In addition to being useful for the production of metabotropic glutamate receptor subtype mGluR6 proteins, these nucleic acids are also useful as probes, thus enabling those skilled in the art, without undue experimentation, to identify and isolate nucleic acids encoding related receptor subtypes.

In addition to disclosing novel metabotropic glutamate receptor protein subtypes, the present invention also comprises methods for using such receptor subtypes to identify and characterize compounds which affect the function of such receptors, e.g., agonists, antagonists, and modulators of glutamate receptor function. The invention also comprises methods for determining whether unknown protein(s) are functional as metabotropic glutamate receptor subtypes.

DETAILED DESCRIPTION OF THE INVENTION

Figure 1:
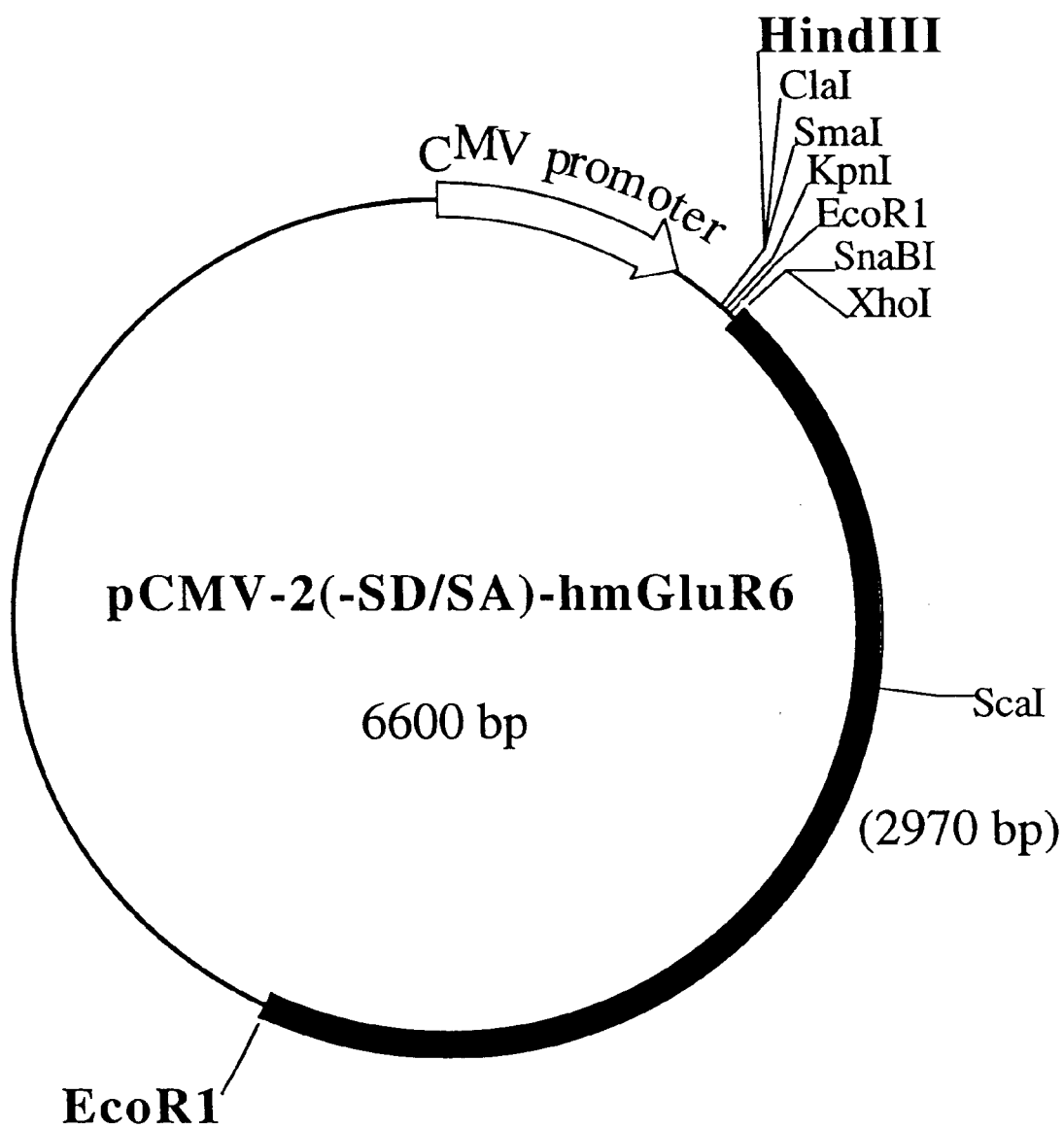
FIG. 1 presents a partial restriction map of a CMV promoter-based mammalian vector containing the mGluR6-encoding DNA and designated pCMV-T7-2(-SD/SA)-hmGluR6.

In accordance with the present invention, there are provided isolated nucleic acids encoding human metabotropic glutamate receptor subtype mGluR6. Also provided are protein(s) encoded by the above-described nucleic acids, as well as antibodies generated against the protein(s). In other aspects of the present invention, there are provided nucleic acid probes comprising metabotropic glutamate receptor subtype-selective portions of the above-described nucleic acids. In a still further aspect, cells containing such nucleic acids and eucaryotic cells expressing such nucleic acids are provided.

As employed herein, the phrase "human metabotropic glutamate receptor subtypes" refers to isolated and/or purified proteins which participate in the G-protein-coupled response of cells to glutamatergic ligands. Such receptor subtypes are individually encoded by distinct genes which do not encode other metabotropic glutamate receptor subtypes (i.e., each subtype is encoded by a unique gene). Complementary DNA clones encoding various human metabotropic glutamate receptor subtypes (e.g., mGluR1, mGluR2, mGluR3, mGluR5) have been isolated. See, for example, WO 94/29449, which is hereby incorporated by reference herein in its entirety. Such receptor subtypes are typically characterized by having seven putative transmembrane domains, preceded by a large putative extracellular amino-terminal domain and followed by a large putative intracellular carboxy-terminal domain. Metabotropic glutamate receptors share essentially no amino acid sequence homology with other G-protein-coupled receptors that are not metabotropic glutamate receptors.

Regarding the inter-relationship between each of the metabotropic glutamate receptor subtypes, the amino acid sequences of mGluR1 receptor subtypes are generally less than about 70% identical to the amino acid sequences of other human metabotropic glutamate receptor subtypes, with identities less than about 45% typically observed. The amino acid sequences of mGluR2 receptor subtypes are generally less than 60% identical to the amino acid sequences of other human metabotropic glutamate receptor subtypes, with identities of less than 45% typically observed. The amino acid sequences of mGluR3 receptor subtypes are generally less than 60% identical to the amino acid sequences of other human metabotropic glutamate receptor subtypes, with identities of less than 45% typically observed. The amino acid sequences of mGluR5 receptor subtypes are generally less than 70% identical to the amino acid sequences of other human metabotropic glutamate receptor subtypes, with identities of less than 45% typically observed. The amino acid sequences of mGluR6 receptor subtypes are generally less than 70% identical to the amino acid sequences of other human metabotropic glutamate receptor subtypes, with identities of less than 40% typically observed.

Also included within the above definition are variants thereof encoded by mRNA generated by alternative splicing of a primary transcript, as well as fragments thereof which retain one or more of the above physiological and/or physical properties.

Use of the terms "isolated" or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of glutamatergic ligands (such as ACPD or ACPD-like ligands, glutamate, L-AP4, L-SOP, and the like) to said receptor protein(s) modifies the receptor interaction with G-proteins, which in turn affects the levels of intracellular second messengers, leading to a variety of physiological effects. Stated another way, "functional" means that a response is generated as a consequence of agonist activation of receptor protein(s).

As used herein, a splice variant refers to variant metabotropic glutamate receptor subtype-encoding nucleic acid(s) produced by differential processing of primary transcript(s) of genomic DNA, resulting in the production of more than one type of mRNA. cDNA derived from differentially processed primary transcript will encode metabotropic glutamate receptor subtypes that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are nucleic acids that encode metabotropic glutamate receptor subtypes as defined above, but that by virtue of degeneracy of the genetic code do not necessarily hybridize to the disclosed nucleic acids under specified hybridization conditions. Such subtypes also form functional receptors, as assessed by methods described herein or known to those of skill in the art. Typically, unless a metabotropic glutamate receptor subtype is encoded by RNA that arises from alternative splicing (i.e., a splice variant), metabotropic glutamate receptor subtype-encoding nucleic acids and the metabotropic glutamate receptor protein encoded thereby share substantial sequence homology with at least one of the metabotropic glutamate receptor subtype nucleic acids (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional metabotropic glutamate receptor subtype.

Exemplary DNA sequences encoding human mGluR6 subtypes are represented by nucleotides which encode substantially the same amino acid sequence as set forth in SEQ ID NO:2, or amino acid sequences that have substantial sequence homology with the amino acid sequence set forth in SEQ ID NO:2. Presently preferred sequences encode the amino acid sequence set forth in SEQ ID NO:2.

An exemplary splice variant of the above-described DNA sequences encodes at least the 22 amino acid residues set forth in SEQ ID NO:4, which at least in part define an alternate 5' portion of mGluR6. Presently preferred splice variants comprise at least the 67 nucleotides set forth in SEQ ID NO:3. Thus, one potential splice variant of mGluR6-encoding DNA comprises nucleotides 896–2961 of SEQ ID NO:1, preceded by nucleotides 1–67 of SEQ ID NO:3.

Exemplary DNA can alternatively be characterized as those nucleotide sequences which encode an human mGluR6 subtype and hybridize under high-stringency conditions to substantially the entire sequence of SEQ ID NO:1, or substantial portions thereof (i.e., typically at least 46 or more contiguous nucleotides thereof).

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C. - 16.6(\log_{10}[Na^+]) + 0.41(\%G+C) - 600/1,$$

where 1 is the length of the hybrids in nucleotides. $T_m$ decreases approximately 1–1.5° C. with every 1% decrease in sequence homology In general., the stability of a hybrid is a function of sodium ion concentration and temperature. Typically, the hybridization reaction is performed under conditions of lower stringency, followed by washes of varying, but higher, stringency Reference to hybridization stringency relates to such washing conditions Thus, as used herein:

(1) HIGH STRINGENCY conditions, with respect to fragment hybridization, refer to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.;

(2) MODERATE STRINGENCY conditions, with respect to fragment hybridization, refer to conditions equivalent to hybridization in 50% formamide, 5× Denhart's solution, 5× SSPE, 0.2% SDS at 42° C., followed by washing in 0.2× SSPE, 0.2% SDS, at 65° C.; and (3) LOW STRINGENCY conditions, with respect to fragment hybridization, refer to conditions equivalent to hybridization in 10% formamide, 5× DenhartDs solution, 6× SSPE, 0.2% SDS at 42° C., followed by washing in 1× SSPE, 0.2% SDS, at 50° C.

(4) HIGH STRINGENCY conditions, with respect to oligonucleotide (i.e., synthetic DNA≦about 30 nucleotides in length) hybridization, refer to conditions equivalent to hybridization in 10% formamide, 5× Denhart's solution, 6× SSPE, 0.2% SDS at 42° C., followed by washing in 1× SSPE, and 0.2% SDS at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50× stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences encoding human mGluR6 subtypes are those which have substantially the same nucleotide sequence as the coding sequences in SEQ ID NO:1; with polynucleic acid having the same sequence as the coding sequence in SEQ ID NO:1 being most preferred As used herein, the phrase "substantial sequence homology" refers to nucleotide sequences which share at least about 90% identity, and amino acid sequences which typically share more than 95% amino acid identity It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantially the same" is used herein in reference to the nucleotide sequence of DNA, the ribonucleotide sequence of RNA, or the amino acid sequence of protein, that have slight and non-consequential sequence variations from the actual sequences disclosed herein. Species that are substantially the same are considered to be equivalent to the disclosed sequences and as such are within the scope of the appended claims. In this regards "slight and non-consequential sequence variations" mean that sequences that are substantially the same as the DNA, RNA, or proteins disclosed and claimed herein are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particulars functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

DNA encoding human metabotropic glutamate receptor subtypes may be isolated by screening suitable human cDNA or human genomic libraries under suitable hybridization conditions with DNA disclosed herein (e.g., nucleotides derived from SEQ ID NOs:1 or 3). Suitable libraries can be prepared from neural tissue samples, e.g., retina tissue, cell lines, and the like. For example, the library can be screened with a portion of DNA including substantially the entire receptor subtype-encoding sequence thereof, or the library may be screened with a suitable oligonucleotide probe based on a portion of the DNA.

As used herein, a probe is single-stranded DNA or RNA that has a sequence of nucleotides that includes at least about 46 contiguous bases that are the same as (or the complement of) any 46 or more contiguous bases set forth in SEQ ID NOs:1 or 3. Preferred regions from which to construct probes include 5' and/or 3' coding sequences, sequences predicted to encode transmembrane domains, sequences predicted to encode cytoplasmic loops, ligand binding sites, and the like.

Either the full-length cDNA clones, fragments thereof, or oligonucleotides based on portions of the cDNA clones can be used as probes, preferably labeled with suitable label means for ready detection. When fragments are used as probes, DNA sequences for such probes will preferably be derived from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982) *J. Mol. Biol.* Vol. 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human metabotropic glutamate receptor protein subtypes, said method comprising:

contacting human DNA with a nucleic acid probe as described above, wherein said contacting is carried out under low- to moderate-stringency hybridization conditions when the probe used is a polynucleic acid fragment, or under high-stringency hybridization conditions when the probe used is an oligonucleotide, and identifying DNA(s) which hybridize to said probe.

After screening the library, positive clones are identified by detecting a hybridization signal; the identified clones are characterized by restriction enzyme mapping and/or DNA sequence analysis, and then examined by comparison with the sequences set forth herein to ascertain whether they include DNA encoding a complete metabotropic glutamate receptor subtype (i.e., if they include translation initiation and termination codons) If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and deduced amino acid sequences provided herein.

The mGluR6-encoding DNA clones provided herein may be used to isolate genomic clones encoding the mGluR6 subtype and to isolate any splice variants by screening libraries prepared from different neural tissues. Nucleic acid amplification techniques, which are well known in the art, can be used to locate DNA encoding splice variants of human metabotropic glutamate receptor subtypes. This is accomplished by employing oligonucleotides based on DNA sequences surrounding predicted intron/exon boundaries as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that may correspond to different splice variants of transcripts encoding human metabotropic glutamate receptor subtypes.

It has been found that not all metabotropic glutamate receptor subtypes (and variants thereof) are expressed in all neural tissues or in all portions of the brain. Thus, in order to isolate cDNA encoding a particular subtype (or splice variants thereof), it is preferable to screen libraries prepared from different neuronal or neural tissues or cells. Preferred libraries for obtaining DNA encoding each subtype include:

cerebellum to isolate human mGluR1-encoding DNAs;

hippocampus to isolate human mGluR2-encoding DNAs;

hippocampus and cerebellum to isolate mGluR3-encoding DNAs;

hippocampus and cerebellum to isolate mGluR5-encoding DNAs;

retina to isolate mGluR6-encoding DNAs; and the like.

Once DNA encoding a particular receptor subtype has been isolated, ribonuclease (RNase) protection assays can be employed to determine which tissues express mRNA encoding such subtype (or splice variant thereof). These assays provide a sensitive means for detecting and quantitating an RNA species in a complex mixture of total cellular RNA. The subtype DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. In situ hybridization techniques can also be used to determine which tissues express mRNAs encoding particular metabotropic glutamate receptor subtypes. Thus, labeled subtype DNAs can be hybridized to different brain region slices to visualize subtype mRNA expression.

The distribution of expression of some human metabotropic glutamate receptor subtypes may differ from the distribution of such receptors in rat. For example, even though RNA encoding the rat mGluR5 subtype is abundant in rat hippocampus, but is not abundant in rat cerebellum [see, e.g., Abe et al., J. Biol. Chem. 267: 13361–13368 (1992)], human mGluR5-encoding cDNAs were successfully obtained from human cerebellum cDNA libraries.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

An expression vector includes vectors capable of expressing DNAs that are operatively linked with regulatory sequences, such as promoter regions, that are capable of regulating expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention metabotropic glutamate receptor subtypes in eukaryotic host cells, particularly mammalian cells, include cytomegalovirus (CMV) promoter-containing vectors such as pCMV-T7-2(-SD/SA) and pCMV-T7-3(-SD/SA), pcDNA3, and the like, as well as SV40 promoter-containing vectors and MMTV LTR promoter-containing vectors, such as pMMTVT7(+) or pMMTVT7(-) (modified versions of pMAMneo (Clontech, Palo Alto, Calif.), prepared as described herein), and the like.

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' and/or 3' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. Likewise, alternative codons, encoding the same amino acid, can be substituted for coding sequences of the metabotropic glutamate receptor subunits in order to enhance transcription (e.g., the codon preference of the host cells can be adopted, the presence of G-C rich domains can be reduced, and the like). Furthermore, for potentially enhanced expression of metabotropic glutamate receptor subunits in amphibian oocytes, the subunit coding sequence can optionally be incorporated into an expression construct wherein the 5'- and 3'-ends of the coding sequence are contiguous with Xenopus β-globin gene 5' and ₃' untranslated sequences, respectively. For example, metabotropic glutamate receptor subunit coding sequences can be incorporated into vector pSP64T (see Krieg and Melton (1984) in Nucleic Acids Research 12:7057–7070) a modified form of pSP64 (available from Promega, Madison, Wis.). The coding sequence is inserted between the 5' end of the β-globin gene and the 3' untranslated sequences located downstream of the SP6 promoter. In vitro transcripts can then be generated from the resulting vector. The desirability of (or need for) such modifications may be empirically determined.

As used herein, expression refers to the process by which polynucleic acids are transcribed into mRNA and translated into peptides, polypeptides, or proteins If the polynucleic acid is derived from genomic DNA, expression may, if an appropriate eukaryotic host cell or organism is selected, include splicing of the mRNA.

Particularly preferred base vectors which contain regulatory elements that can be linked to human metabotropic receptor-encoding DNAs for transfection of mammalian cells are cytomegalovirus (CMV) promoter-based vectors such as pCMV-T7-2(-SD/SA) and pCMV-T7-3(-SD/SA) (described herein) or pcDNA3 (Invitrogen, San Diego, Calif.), MMTV promoter-based vectors such as pMMTVT7 (+) or pMMTVT7(–) (as described herein), and SV40 promoter-based vectors such as pSVβ (Clontech, Palo Alto, Calif.).

Full-length DNAs encoding human metabotropic glutamate receptor subtypes can be inserted into vectors pMMTVT7(+), pMMTVT7(–), pCMV-T7-2(-SD/SA) or pCMV-T7-3(-SD/SA). pCMV-T7-2(-SD/SA) (and pCMV-T7-3(-SD/SA)) are pUC19-based mammalian cell expression vectors containing the CNV promoter/enhancer, a T7 bacteriophage RNA polymerase promoter positioned downstream of the promoter, followed by an SV40 polyadenylation signal and a polylinker between the T7 promoter and the polyadenylation signal. Placement of metabotropic glutamate receptor subtype DNA between the CMV promoter and SV40 polyadenylation signal should provide for constitutive expression of the foreign DNA in a mammalian host cell transfected with the construct.

Vectors pMMTVT7(+) and pMMTVT7(–) were prepared by modifying vector pMAMneo (Clontech, Palo Alto, Calif.). pMAMneo is a mammalian expression vector that contains the Rous Sarcoma Virus (RSV) long terminal repeat (LTR) enhancer, linked to the dexamethasone-inducible mouse mammary tumor virus (MMTV)-LTR promoter, followed by SV40 splicing and polyadenylation sites. pMAMneo also contains the *E. coli* neo gene for selection of transformants, as well as the β-lactamase gene (encoding a protein which imparts ampicillin-resistance) for propagation in *E. coli*.

Vector pMMTVT7(+) can be generated by modification of pMAMneo to remove the neo gene and insert the multiple cloning site and T7 and T3 promoters from pBluescript (Stratagene, La Jolla, Calif.). Thus, pMMTVT7(+) contains the RSV-LTR enhancer linked to the MMTV-LTR promoter, a T7 bacteriophage RNA polymerase promoter positioned downstream of the MMTV-LTR promoter, a polylinker positioned downstream of the T7 promoter, a T3 bacteriophage RNA polymerase promoter positioned downstream of the T7 promoter, and SV40 splicing and polyadenylation sites positioned downstream of the T3 promoter. The β-lactamase gene (encoding a protein which imparts ampicillin-resistance) from pMAMneo is retained in pMMTVT7(+), although it is incorporated in the reverse orientation relative to the orientation in pMAMneo.

Vector pMMTVT7(–) is identical to pMMTVT7(+) except that the positions of the T7 and T3 promoters are switched, i.e., the T3 promoter in pMMTVT7(–) is located where the T7 promoter is located in pNMTVT7(+), and the T7 promoter in pMMTVT7(–) is located where the T3 promoter is located in pMMTVT7(+). Therefore, vectors pMMTVT7(+) and pMMTVT7(–) contain all of the regulatory elements required for expression of heterologous DNA in a mammalian host cell, wherein the heterologous DNA has been incorporated into the vectors at the polylinker. In addition, because the T7 and T3 promoters are located on either side of the polylinker, these plasmids can be used for synthesis of in vitro transcripts of heterologous DNA that has been subcloned into the vectors at the polylinker.

For inducible expression of human metabotropic glutamate receptor subtype-encoding DNA in a mammalian cell, the DNA can be inserted into a plasmid such as pMMTVT7(+) or pMMTVT7(–). These plasmids contain the mouse mammary tumor virus (MMTV) LTR promoter for steroid-inducible expression of operatively associated foreign DNA. If the host cell does not express endogenous glucocorticoid receptors required for uptake of glucocorticoids (i.e., inducers of the MMTV LTR promoter) into the cell, it is necessary to additionally transfect the cell with DNA encoding the glucocorticoid receptor (ATCC accession no. 67200). For synthesis of in vitro transcripts, the human mGluR cDNA can also be subcloned into pIBI24 (International Biotechnologies, Inc., New Haven, Conn.), pCMV-T7-2(-SD/SA) or pCMV-T7-3(-SD/SA), pMMTVT7 (+), pMMTVT7(–), pBluescript (Stratagene, La Jolla, Calif.), pGEM7Z (Promega, Madison, Wis.), or the like.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g, Sambrook et al. (1989) *Molecular Cloning. A Laboratory Manual*, Second Edition, Cold Spring Harbor Laboratory Press) Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subtype(s) encoded by the DNA is (are) expressed. Preferred cells include mammalian cells (e.g., HEK293, CHO, BHK, GH3 and Ltk⁻ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929, 555 and 4,855,231), *Saccharomyces cerevisiae, Candida tropicalis, Hansenula polymorpha*, and the like), mammalian expression systems, including commercially available systems and other such systems known to those of skill in the art which express G-proteins (either endogenously or recombinantly), for expression of DNA encoding the human metabotropic glutamate receptor subtypes provided herein are presently preferred. Xenopus oocytes are preferred for expression of in vitro mRNA transcripts of DNA encoding those human metabotropic receptor subtypes that are coupled to the PI hydrolysis/$Ca^{++}$ signalling pathways. An endogenous inositol triphosphate second messenger-mediated pathway in oocytes permits functional expression of the subclass of inositol triphosphate pathway-linked human metabotropic receptors in these cells. Oocytes expressing recombinant human metabotropic receptors respond to agonists via the oocyte G-protein-coupled $IP_3$ generation pathway, which stimulates release of $Ca^{++}$ from internal stores, and reportedly activates a chloride channel that can be detected as a delayed oscillatory current by voltage-clamp recording.

Host cells for functional recombinant expression of human metabotropic receptors preferably express endogenous or recombinant guanine nucleotide-binding proteins (i.e., G-proteins). G-proteins are a highly conserved family of membrane-associated proteins composed of $\alpha$, $\beta$ and $\gamma$ subunits. The $\alpha$ subunit, which binds GDP and GTP, differs in different G-proteins. The attached pair of $\beta$ and $\gamma$ subunits may or may not be unique; different $\alpha$ chains may be linked to an identical $\beta\gamma$ pair or to different pairs [Linder and Gilman, Sci. Am. 267:56–65 (1992)]. More than 30 different cDNAs encoding G protein $\alpha$ subunits have been cloned [Simon et al., Science 252:802 (1991)]. Four different $\beta$ polypeptide sequences are known [Simon et al., Science 252:802 (1991)]. Three of five identified $\gamma$ cDNAs have been cloned [Hurley et al., PNAS U.S.A. 81:6948 (1984); Gautam et al., Science 244:971 (1989); and Gautam et al., PNAS U.S.A. 87:7973 (1990)]. The sequences of a fourth $\gamma$ cDNA [Kleuss et al., Science 259:832 (1993)] and a fifth $\gamma$ cDNA [Fisher and Aronson, Mol. Cell. Bio. 12:1585 (1992)] have been established, and additional $\gamma$ subtypes may exist [Tamir et al., Biochemistry 30:3929 (1991)]. G-proteins switch between active and inactive states by guanine nucleotide exchange and GTP hydrolysis. Inactive G protein is stimulated by a ligand-activated receptor to exchange GDP for GTP. In the active form, the $\alpha$ subunit, bound to GTP, dissociates from the $\beta\gamma$ complex, and the subunits then interact specifically with cellular effector molecules to evoke a cellular response. Because different G-proteins can interact with different effector systems (e.g., phospholipase C, adenyl cyclase systems) and different receptors, it is useful to investigate different host cells for expression of different recombinant human metabotropic receptor subtypes. Alternatively, host cells can be transfected with G-protein subunit-encoding DNAs for heterologous expression of differing G proteins.

In preferred embodiments, human metabotropic glutamate receptor subtype-encoding DNA is ligated into a vector, and introduced into suitable host cells to produce transformed cell lines that express a specific human metabotropic glutamate receptor subtype, or specific combinations of subtypes. The resulting cell lines can then be produced in quantity for reproducible quantitative analysis of the effects of known or potential drugs on receptor function. In other embodiments, mRNA may be produced by in vitro transcription of DNA encoding each subtype. This mRNA, either from a single subtype clone or from a combination of clones, can then be injected into Xenopus oocytes where the mRNA directs the synthesis of functional human metabotropic glutamate receptor subtypes. Alternatively, the subtype-encoding DNA can be directly injected into oocytes for expression of functional human metabotropic glutamate receptor subtypes. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected and which cells express (endogenously or recombinantly) G-proteins. Preferred cells are those that express little, if any, endogenous metabotropic receptors and can be transiently or stably transfected and also express invention DNA and RNA. Presently most preferred cells are those that can form recombinant or heterologous human metabotropic glutamate receptors comprising one or more subtypes encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, baby hamster kidney (BHK) cells, rat pituitary tumor (GH3) cells, African green monkey cells and other such cells known to those of skill in the art), amphibian cells (e.g., *Xenopus laevis* oöcytes), yeast cells (e.g., *Saccharomyces cerevisiae, Pichia pastoris*), and the like. Exemplary cells for expressing injected RNA transcripts include *Xenopus laevis* oöcytes. Cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); CHO cells (which are available from ATCC under accession #CRL9618, CCL61 or CRL9096); DG44 cells (dhf⁻ CHO cells; see, e.g., Urlaub et al. (1986) Cell. Molec. Genet. 12: 555); GH3 cells (available from the ATCC under accession #CCL82.1) and BHK cells (see Waechter and Baserga, PNAS U.S.A. 79:1106–1110 (1982); also available from ATCC under accession #CRL6281). Presently preferred cells include CHO cells and HEK293 cells, particularly HEK293 cells that can be frozen in liquid nitrogen and then thawed and regrown (for example, those described in U.S. Pat. No. 5,024,939 to Gorman (see, also, Stillman et al. (1985) Mol. Cell. Biol. 5:2051–2060)), DG44, Ltk⁻ cells, and the like. Those of skill in the art recognize that comparison experiments should also be carried out with whatever host cells are employed to determine background levels of glutamate production induced by the ligand employed, as well as background levels of glutamate present in the host cell in the absence of ligand.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

To produce such stably or transiently transfected cells, the cells should be transfected with a sufficient concentration of subtype-encoding nucleic acids to form human metabotropic glutamate receptors indicative of the human subtypes encoded by the heterologous DNA. The precise amounts of DNA encoding the subtypes may be empirically determined and optimized for a particular subtype, cells and assay conditions. Recombinant cells that express metabotropic glutamate receptors containing subtypes encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human metabotropic glutamate receptor subtypes may be purified using protein purification methods known to those of skill in the art. For example, antibodies or other ligands that specifically bind to one or more subtypes may be used for affinity purification of a given metabotropic glutamate receptor subtype.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human metabotropic glutamate receptor subtype, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Those of skill in the art can readily identify a variety of assays which can be used to detect the expression of functional mGluRs. Examples include PI turnover assays [see, e.g., Nakajima et al., J. Biol. Chem. 267:2437–2442 (1992) and Example 3.C.2], adenylate cyclase assays, cAMP assays [see, e.g., Nakajima et al., supra and Example 3.C.4.], calcium ion flux assays [see, e.g., Ito et al., J. Neurochem. 56:531–540 (1991) and Example 3.C.1], cGMP assays [see, e.g., Steiner et al., J. Biol. Chem 247:1106–1113 (1972)], cGMR-specific phosphodiesterase assays [see, e.g., Lieb-man et al., Meth. Enzymol. 81:532–542 (1982)], arachidonic acid release assays [see, e.g., Felder et al., J. Biol. Chem. 264:20356–20362 (1989)], and the like. Methods of analyzing changes in intracellular $Ca^{2+}$ and cyclic nucleotide concentrations are known to those of skill in the art. One such method involves co-transfection of mGluR-expressing cells with a $Ca^{2+}$—and/or cyclic nucleotide-responsive gene promoter linked to DNA encoding a reporter molecule (e.g., luciferasel chloramphenicol acetyltransferase, and the like). Activation of the mGluRs expressed in such cells is detected as a change in reporter gene transcription or product. Such methods for evaluating signal transduction mediated via $Ca^{2+}$ and cyclic nucleotide level changes are described in commonly assigned pending U.S. patent application Ser. No. 07/563,751, U.S. Pat. No. 5,401,629 and Ser. No. 07/962,238 U.S. Pat. No. 5,436,128 and corresponding PCT application No. US91/05625.

In addition, cation-based assays (as described herein) can be employed for monitoring receptor-induced changes in intracellular cyclic nucleotide levels. Such assays employ host cells expressing cyclic nucleotide-gated ion channels. These channels, which occur in, for example, rod photoreceptor cells, olfactory cells and bovine kidney cells (see, for example, Kaupp et al., in Nature 342:762–766 (1989), with reference to EMBL accession no. X51604; Dhallan et al., in Nature 347:184–187 (1990), with reference to EMBL accession no. X55519; and Biel et al., in Proc. Natl. Acad. Sci. USA 91:3505–3509 (1994), with reference to EMBL accession no. X59668, respectively), are permeable to cations upon activation by binding of cAMP or cGMP. Thus, in assays useful in the practice of the present invention, host cells expressing endogenous or recombinant cyclic nucleotide-gated channels are transfected (or injected) with nucleic acids encoding receptors suspected of influencing cyclic nucleotide levels (e.g., metabotropic glutamate receptor-encoding DNA), and then monitored for changes in the amount of cyclic nucleotide activation of the channels. Measuring changes in cyclic nucleotide activation of channels allows one to indirectly identify as functional those receptors that cause a change in cAMP or cGMP levels when activated. The change in the amount of activation of the cyclic nucleotide-gated channels can be determined by measuring ion flux through the channel either by electrophysiological measurement of currents or by measuring a change in intracellular cation levels (e.g., by fluorescence measurement of intracellular calcium).

In assays of cells expressing receptor species that cause a decrease in cyclic nucleotides upon activation (e.g., some metabotropic glutamate receptors), it may be preferable to expose the cells to agents that increase intracellular levels of cyclic nucleotides (e.g., forskolin and 3-isobutyl-1-methylxanthine (IBMX)) prior to adding a receptor-activating compound to the cells in the assay.

Host cells suitable for use in the above-described assay include any host cells suitable for expression of the receptor being studied (e.g., L cells, HEK293 cells, CHO cells or Xenopus oocytes for assays of metabotropic glutamate receptors). The cells can be sequentially transfected (or injected) with nucleic acids encoding a cyclic nucleotide-gated channel and receptor-encoding nucleic acids, or the cells can be co-transfected with the two nucleic acids. Transient or stable transfectione as described in Examples 3A and 3B, can be carried out.

Cells transfected (or injected) with cyclic nucleotide-gated channel nucleic acid are incubated (typically for ~24–48 hours) before testing for function. The activity of the channels can be assessed using inside-out membrane patches pulled from the transfected cells (so that the concentration of CAMP reaching the cytoplasmic face can be controlled) The transfectants can also be analyzed by single-cell video imaging or automated fluorescence analysis of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay can be conducted essentially as described in Example 3.C.4.b, and the automated fluorescence assay can be conducted as described in Example 3.c.1.

Cation-based assays can also be used to monitor activation and inhibition of mGluRs that are coupled to G-proteins that also couple to voltage-gated ion channels, e.g., calcium channels Interaction of such mGluRs with G-proteins results in opening or typically closing of the ion channel, which can be detected through electrophysiological or $Ca^{2+}$-sensitive indicator-based assays of ion flux. When the function of this class of mGluRs is to be analyzed through measurement of cation flux, the host cell used for expression of the recombinant mGluRs must also express endogenous or heterologous voltage-gated ion channels, preferably calcium channels (see, for example, commonly assigned pending U.S. patent application Ser. Nos. 07/482,384, 07/914,231, 07/745,206, 08/105,536, 08/149,097, 08/311,363, 08/314,083, 08,193,078, 08/223,305 and 08/290,012 and corresponding PCT application nos. US89/01408, US92/06903 and US91/01124). Thus, to examine possible mGluR6 regulation of voltage-gated calcium channels, cells transfected with DNA encoding mGluR6 can be co-transfected with DNA encoding voltage-gated calcium channel subunits (e.g., L-type, N-type or P-type channels) and analyzed for calcium channel activity under various conditions. For example, the currents generated upon membrane depolarization (either through voltage pulse or exposure to $K^+$) before and after incubation of the cells with agonist (e.g., glutamate, L-AP4 or L-SOP) can be compared. Functional coupling of the mGluR6 receptor to voltage-gated calcium channels would be revealed as a change (e.g., decrease) in the current measured in the presence of agonist relative to current measured in the absence of agonist. It is also possible that mGluRs that cause a change in intracellular second messenger systems, e.g., cyclic nucleotide levels, may indirectly regulate voltage-gated calcium channel activity (e.g., via protein kinases, and the like). Functional analysis of these mGluRs can also be accomplished through examination of mGluR agonist effects on calcium channel activity in cells co-expressing recombinant mGluRs and voltage-gated calcium channels, as described above.

The DNA, mRNA, vectors, receptor subtypes, and cells provided herein permit production of selected metabotropic glutamate receptor subtypes, as well as antibodies to said receptor subtypes. This provides a means to prepare synthetic or recombinant receptors and receptor subtypes that are substantially free of contamination from many other receptor proteins whose presence can interfere with analysis of a single metabotropic glutamate receptor subtype. The availability of desired receptor subtypes makes it possible to observe the effect of a drug substance on a particular receptor subtype or combination of metabotropic glutamate receptor subtypes, and to thereby perform initial in vitro screening of the drug substance in a test system that is specific for humans and specific for a human metabotropic glutamate receptor subtype or combination of metabotropic glutamate receptor subtypes. The availability of specific antibodies makes it possible to identify the subtype combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subtypes or specific combinations of various receptor subtypes with a variety of potential agonists or antagonists provides additional information with respect to the function and activity of the individual subtypes and should lead to the identification and design of compounds that are capable of very specific interaction with one or more receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human metabotropic glutamate receptor subtypes enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

Invention DNA and mutants thereof may also be expressed in non-human transgenic animals to facilitate the analysis of mGLuRs and their role in normal and pathological function of the CNS. Methods of generating transgenic animals are well known in the art (see, e.g., Hammer et al., in Nature 315:680–683 (1985)).

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if endogenous channels are in turn activated. If currents (or alterations in currents present in the absence of ligand) are detected, the fragments are functional as glutamate receptors.

In accordance with still another embodiment of the present invention, there is provided a method for identifying compounds which bind to human metabotropic glutamate receptor subtype mGluR6, said method comprising employing receptor proteins of the invention in a competitive binding assay. Such an assay can accommodate the rapid screening of a large number of compounds to determine which compounds, if any, are capable of displacing specifically bound [$^3$H] glutamate or [$^3$H]-L-AP4 or the like, i.e., binding to metabotropic glutamate receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor subtype(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human metabotropic glutamate receptor subtype mGluR6 of the invention, said bioassay comprising (a) exposing cells containing DNA encoding human metabotropic glutamate receptor subtype(s), wherein said cells express functional metabotropic glutamate receptors, to at least one compound whose ability to modulate the activity of said receptors is sought to be determined; and thereafter (b) monitoring said cells for changes in second messenger activity.

The above-described bioassay enables the identification of agonists, antagonists and allosteric modulators of human metabotropic glutamate receptor subtype mGluR6. According to this method, recombinant metabotropic glutamate receptors are contacted with an "unknown" or test substance (in the further presence of a known metabotropic glutamate agonist, when antagonist activity is being tested), the second messenger activity of the known glutamate receptor is monitored subsequent to the contact with the "unknown" or test substance, and those substances which increase or decrease the second messenger response of the known glutamate receptor(s) are identified as functional ligands (i.e., modulators, agonists or antagonists) for human metabotropic glutamate receptors. Second messenger activities which can be monitored include changes in the concentration of intracellular calcium ions, $IP_3$, cAMP and cGMP levels, or monitoring of arachidonic acid release or activation or inhibition of ion current (when the host cell expresses ion channels responsive to the second messenger activities).

In accordance with a particular embodiment of the present invention, recombinant human metabotropic glutamate receptor-expressing mammalian cells or oocytes can be contacted with a test compound, and the modulating effect(s) thereof can then be evaluated by comparing the metabotropic glutamate receptor-mediated response in the presence and absence of test compound, or by comparing the metabotropic glutamate receptor-mediated response of test cells, or control cells (i.e., cells that do not express metabotropic glutamate receptors), to the presence of the compound.

As used herein, a compound or signal that "modulates the activity of a metabotropic glutamate receptor subtype" refers to a compound or signal that alters the activity of metabotropic glutamate receptors so that activity of the metabotropic glutamate receptor is different in the presence of the compound or signal than in the absence of the compound or signal. In particular, such compounds or signals include agonists and antagonists. The term agonist refers to a substance or signal, such as glutamate, L-2-amino-4-phosphonobutyrate (L-AP4), 1-amino-cyclopentyl-1,3-dicarboxylic acid (ACPD) or L-serine-O-phosphate (L-SOP), that activates receptor function; and the term antagonist refers to a substance that blocks agonist-induced receptor activation. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human metabotropic glutamate receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express the recombinant human metabotropic glutamate receptor subtype(s), expressed in the transfected cells. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the second messenger activity of human metabotropic glutamate receptors can be modulated by contacting such receptors with an effective amount of at least one compound identified by the above-described bioassay. In accordance with yet another embodiment of the present invention, there are provided antibodies generated against the above-described receptor proteins. Such antibodies can be employed for studying receptor tissue localization, subtype composition, structure of functional domains, purification of receptors, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the metabotropic glutamate receptor subtypes for use as immunogen (as either a synthetic peptide or a recombinantly produced bacterial fusion protein) include antigenicity, accessibility (i.e., extracellular and cytoplasmic domains), uniqueness to the particular subtype, etc.

The availability of subtype-specific antibodies makes possible the application of the technique of immunohistochemistry to monitor the distribution and expression density of various subtypes (e.g., in normal vs diseased brain tissue). Such antibodies could also be employed for diagnostic and therapeutic applications.

In accordance with still another embodiment of the present invention, there are provided methods for modulating the second messenger activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention will now be described in greater detail by reference to the following non-limiting examples.

EXAMPLE 1

Isolation of DNA Encoding Human Metabotropic Glutamate Receptor Subtype mGluR6 cDNA Library Screening

A 0.6-kb PstI human cDNA fragment having some homology to nucleotides 1483–2110 of the rat mGluR6 cDNA [Nakajima et al. (1993). *J. Biol. Chem.* 266:11868–11873] was used in efforts to obtain a full length human mGluR6 clone. Thus, an amplified random- and oligo(dt)-primed λgt10 human retinal cDNA library ($1 \times 10^6$ recombinants; Clontech, Palo Alto, Calif.) was screened for hybridization to the above-identified fragment. Hybridization was performed in 50% formamide, 5× Denhart's solution, 5× SSPE, 0.2% SDS at 42° C. and the filters were washed in 0.2× SSPE, 0.2% SDS at 65° C.

The inserts of the hybridizing purified plaques were characterized by restriction enzyme mapping and DNA sequence analysis. Two of the hybridizing clones (METAB72 and METAB75) were nearly identical ~2.1-kb fragments and contained a translation termination codon, but no translation initiation codon. Clone METAB75 differs from METAB72 at the 5' end in that METAB75 contains 67 nucleotides (see SEQ ID NO:3) which are not present in METAB72. These 67 nucleotides may represent alternative splicing of the mGluR6 primary transcript. To elucidate the structure of potential splice variants, oligonucleotides corresponding to the 5' and 3' ends of the 67 nucleotide sequences as well as oligonucleotides corresponding to sequence located in the 5' and 3' regions of the mGluR6 cDNA, could be used in nucleic acid amplification of human genomic DNA. Alternatively, human genomic DNA can be screened for hybridization to the 67 nucleotide sequence, and any resulting hybridizing clone(s) analyzed.

To obtain DNA corresponding to the 5' end of the mGluR6 cDNA, a specifically-primed human retinal cDNA library was constructed and the resulting cDNAs were cloned into the λgt10 phage vector. An oligonucleotide corresponding to the antisense of nt 1142 to 1167 in SEQ ID NO:1 was used to prime first-strand cDNA synthesis from human retinal polyA$^+$ RNA. Approximately $1.6 \times 10^6$ recombinants from the λgt10 library were screened for hybridization to a 0.6-kb SmaI fragment from METAB75 using a washing stringency of 0.2× SSPE, 0.2% SDS; 65° C. Twenty hybridizing plaques were identified in this screening, and nine putative human mGluR6 clones (METAB77 to METAB85) were isolated.

DNA sequence analysis of clones METAB84 and METAB85 revealed that they both contain the translation initiation codon. The 3' ends of these clones overlap the 5' end of METAB75.

Preparation of Full-Length mGluR6 cDNA Constructs

A full-length construct encoding the complete human mGluR6 was generated and incorporated into an expression vector for use in preparing in vitro transcripts of the cDNA and/or expression of the cDNA in mammalian cells. The base expression vector typically used is pCMV-T7-3(-SD/SA) or pCMV-T7-2(-SD/SA). Plasmid pCMV-T7-2(-SD/SA) is a pUC19-based vector that contains a cytomegalovirus (CMV) promoter/enhancer, a T7 bacteriophage RNA polymerase promoter positioned downstream of the CHV promoter/enhancer, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. pCMV-T7-2(-SD/SA) and pCMV-T7-3(-SD/SA) differ only in the orientation of the restriction sites in the polylinker.

To prepare a full-length mGluR6 construct (see SEQ ID NO:1), portions of clones METAB75 and METAB85 were ligated together. Initially, the inserts of METAB75 and METAB85 were separately transferred from λgt10 as EcoRI fragments into EcoRI-digested pGEM-7Zf (Promega, Madison, Wis.) for ease of manipulation. The pGEM-7Zf vector containing the METAB85 insert was digested with EcoRI/ScaI to release a 1.0-kb fragment containing the 5' portion of the mGluR6 cDNA (nucleotides 39–1108 of SEQ ID NO:1). The pGEM-7Zf vector containing the insert of METAB75 was digested with ScaI/HindIII to release a 2.0-kb fragment containing the 3' portion of the mGluR6 cDNA (nucleotides 1109–2961 of SEQ ID NO:1), and this fragment was ligated with the 10-kb fragment from METAB85 and EcoRI/HindIII-digested pCMV-T7-2 (-SD/SA) to create pCMV-2 (-SD/SA) -hmGluR6 (see FIG. 1).

In summary, construct pCMV-2(-SD/SA)-hmGluR6 contains 46 bp of $_5$' untranslated sequence from METAB85 (nucleotides 39–84 of SEQ ID NO:1) and a complete coding sequence (nucleotides 85–2718 of SEQ ID NO:1) for the mGluR6 receptor, as well as 243 bp of 3' untranslated sequence (nucleotides 2719–2961 of SEQ ID NO:1). The mGluR6-encoding sequence is operatively linked to the regulatory elements in pCMV-T7-2(-SD/SA) for use in expressing the receptor in mammalian host cells and for use in generating in vitro transcripts of the DNA to be expressed in Xenopus oocytes.

EXAMPLE 2

Expression of Recombinant Human Metabotropic Glutamate Receptors in Oocytes

Xenopus oocytes are injected with in vitro transcripts prepared from constructs containing DNA encoding human metabotropic receptors. Electrophysiological measurements of the oocyte transmembrane currents are made using the two-electrode voltage clamp technique (see e.g., Stuhmer (1992) *Meth. Enzymol.* 207:319–339).

A. Preparation of In Vitro Transcripts

Recombinant capped transcripts of metabotropic receptor cDNAs contained in construct PCMV-2(-SD/SA)-hmGluR6 can be synthesized from linearized plasmids using the Megascript Kit (Cat. #1334, Ambion, Inc., Austin, Tex.). The mass of each synthesized transcript is determined by UV absorbance and the integrity of each transcript is determined by electrophoresis through an agarose gel.

B. Electrophysiology

Xenopus oocytes are injected with 10–50 ng of metabotropic receptor transcripts per oocyte. In order to detect functional expression of mGluRs that, upon activation, induce a decrease in cyclic nucleotide levels and/or directly couple to ion channels, the oocytes can also be injected with transcripts encoding ion channels, e.g., transcripts prepared from DNA encoding cyclic-nucleotide-gated cation channels or voltage-gated calcium channels. The preparation and injection of oocytes are carried out as described by Dascal [(1987) *Crit. Rev. Biochem.* 22:317–387]. Two-to-six days following mRNA injection, the oocytes are examined using the two-electrode voltage clamp technique. The cells are bathed in Ringer's solution (115 mM NaCl, 2.5 mM KCl, 1.8 mM CaCl$_2$, 10 mM HEPES, pH 7.3), and the membrane potential is clamped at −80 to −100 mV. Drugs are applied by continuous bath perfusion at a flow rate of 5–10 ml/min. Data are sampled at 5–100 Hz with a Labmaster or Digidata data acquisition board in PC-386 using AXOTAPE version 2.0 (Axon Instruments, Foster City, Calif.) or PClamp 6.02 software. Data are exported to a laser printer or plotted and analyzed using Prizm version 1.2.

Metabotropic receptor-modulating compounds, i.e., 0.1–1000 μM L-serine-O-phosphate (L-SOP), 0.1–1000 μM glutamate and 0.1–1000 μM L-2-amino-4-phosphonobutyrate (L-AP4) are applied to the bath and the transmembrane currents before and after application are recorded. Upon activation of the recombinant mGluRs, a change in the magnitude and/or biophysics of the current is detected relative to the current measured in the absence of agonist. Activation of mGluRs that cause a decrease in cyclic nucleotide levels typically results in a decrease in the magnitude of the current. Dose-response studies in which the currents measured after application of varying amounts of agonist are compared are thus expected to reveal that the current magnitude decreases with increasing concentration of agonist. Analysis of these data enables a calculation of $EC_{50}$ values for each compound which is used in determining the relative potencies of the compounds.

EXAMPLE 3

Recombinant Expression of Human Metabotropic Glutamate Receptor Subunits in Mammalian Cells Mammalian cells, e.g., human embryonic kidney (HEK 293), baby hamster kidney (BHK), Ltk⁻, GH3 and Chinese hamster ovary (CHO) cells (ire, DG44 cells; see Urlaub et al. (1986) *Som. Cell. Molec. Genet.* 12:555), are transfected with DNA encoding human metabotropic receptors. Transfectants are analyzed for expression of metabotropic receptors using various assays, e.g., cAMP assays, cGMP assays, adenylate cyclase assays, phosphodiesterase assays, inositol phosphate ($IP_1$) assays, $Ca^{++}$-sensitive fluorescent indicator-based assays, and [$^3$H]-glutamate and [$^3$H]-L-AP4 binding assays.

A. Transient Transfection of Mammalian Cells

Mammalian host cells are transiently transfected with DNA encoding mGluR6. Approximately $2\times10^6$ cells are transiently transfected with 5–18 μg of the mGluR6 DNA-containing plasmid according to standard $CaPO_4$ transfection procedures [see Wigler et al. (1979) *Proc. Natl. Acad. Sci. USA* 76:1373–1376]. In addition, 0.5–2 μg of plasmid pCMVβgal (Clontech Laboratories, Palo Alto, Calif.), which contains the *Escherichia coli* β-galactosidase gene fused to the CMV promoter, are co-transfected as a reporter gene for monitoring the efficiency of transfection. As a positive control for the efficiency of transfection, the transfectants are analyzed for β-galactosidase expression by direct staining of the product of a reaction involving β-galactosidase and the X-gal substrate [Jones (1986) EMBO 5:3133–3142]. Transfectants can also be analyzed for β-galactosidase expression by measurement of β-galactosidase activity [Miller (1972) in *Experiments in Molecular Genetics*, pp.352–355, Cold Spring Harbor Press].

If the cells that are transiently transfected with hmGluR6 DNA linked to the MMTV promoter for inducible expression of mGluR6 do not express, or express only low levels of endogenous glucocorticoid receptors, they can be co-transfected with 5 μg of pRShGR (ATCC accession no 67200) which contains DNA encoding a glucocorticoid receptor operatively linked to the Rous Sarcoma virus (RSV) LTR promoter. Co-expression of glucocorticoid receptors in these cells should insure that induction of expression of the MMTV promoter-mGluR6 cDNA occurs upon addition of glucocorticoids (e.g., dexamethasone) to the cells.

The mammalian host cells can also be transiently co-transfected with DNA encoding cyclic nucleotide-gated ion channels or voltage-gated calcium channels. Such cells are particularly useful in evaluating functional expression of mGluRs that cause a decrease in cyclic-nucleotide levels and/or directly couple to ion channels upon activation. Cells expressing both ion channels and mGluRs of this type can be analyzed by ion-flux detection methods, i.e., electrophysiologically or $Ca^{2+}$-sensitive indicator-based assays, to evaluate mGluR function.

The efficiency of transfection of mammalian cells is expected to be typical of standard efficiencies (i.e., ~50%).

B. Stable Transfection of Mammalian Cells

Mammalian cells, such as HEK 293, Ltk⁻, BHK and CHO cells (e.g., DG44 cells), can be stably transfected using the calcium phosphate transfection procedure [*Current Protocols in Molecular Biology*, Vol. 1, Wiley Inter-Science, Supplement 14, Unit 9.1.1–9.1.9 (1990)]. When CHO cells are used as hosts, it is generally preferable to use the SV40 promoter to regulate expression of the human metabotropic receptor-encoding cDNA. Ten-cm plates, each containing $1–2\times10^6$ cells, are transfected with 1 ml of DNA/calcium phosphate precipitate containing approximately 5–10 μg of metabotropic receptor-encoding DNA and 0.5–1 μg of DNA encoding a selectable marker, for example, the neomycin-resistance gene (i.e., pSV2neo) for selection of HEK 293 transformants, the thymidine kinase gene for Ltk⁻ cell transfectants, the dihydrofolate reductase (dhfr) gene for selection of DG44 cell transformants, and the like. After ~14 days of growth in the appropriate selective media, colonies form and are individually isolated using cloning cylinders The isolates are then subjected to limiting dilution and screened to identify those that express metabotropic receptors using, for example, methods described below.

C. Analysis of Transfectants

1. Fluorescent indicator-based assays

Activation of G-protein-coupled metabotropic receptors by agonists leads to stimulation of the phosphatidylinositol (PI) hydrolysis/intracellular $Ca^{++}$ signalling pathway and/or the inhibitory cAMP or cGMP cascade. Additionally, it is possible that some mGluRs can couple to G-proteins that are directly coupled to voltage-gated calcium channels. Because each of these possible effects of mGluR activation can regulate $Ca^{2+}$ levels within the cell, methods of detecting transient changes in intracellular calcium concentration can be applied to the analysis of functional expression of such metabotropic receptors. One method for measuring intracellular calcium levels relies on calcium-sensitive fluorescent indicators.

Calcium-sensitive indicators, such as fluo-3 and fura-2 (Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{++}$ concentration of cells containing the indicator can be expressed directly as an increase in fluorescence (or an increase in the ratio of the fluorescence at two wavelengths when fura-2 is used). An automated fluorescence detection system for assaying metabotropic receptors has been described in commonly assigned pending US patent application Ser. No. 08/229,150 and corresponding PCT Patent Application No. US92/11090, both of which are hereby incorporated by reference herein. Additionally, fluorescence imaging techniques can be utilized to visualize intracellular $Ca^{++}$ oscillations Mammalian cells that are stably or transiently transfected with DNA encoding a human mGlu receptor can be analyzed for expression of functional recombinant metabotropic receptors using the automated fluorescent indicator-based assay and the fluorescence imaging assay. If the mGluR is a type that effects a cellular response through inhibition of adenylate cyclase or cGMP-specific phosphodiesterase, and thereby leads to a decrease in cyclic nucleotide levels, the host cell should also express endogenous or heterologous cyclic nucleotide-gated calcium channels to enable analysis of the mGluR using the fluorescent indicator-based assay (see, for example, Example 3.C.4.b). Likewise, if the mGluR is a type that couples to G-proteins which are directly coupled to voltage-gated calcium channels, the host cell must express endogenous or heterologous voltage-gated calcium channels.

a. Automated fluorescence assay

Untransfected mammalian host cells (or host cells transiently transfected with the base expression vector lacking mGluR-encoding DNA and mammalian host cells that have been transfected with mGluR-encoding DNA are plated in the wells of a 96-well microtiter dish (Nunc Catalog No. 1–6708, distributed by Alameda Industries, Escondido, Calif.) that have been precoated with poly-L-lysine at a density of $2 \times 10^5$ cells/well and loaded with fluo-3 by incubation for 2 hours at 20° C. in a medium containing 20 $\mu$M fluo-3, 0.2% Pluronic F-127 in HBS (125 mM NaCl, 5 mM KCl, 1.8 mM $CaCl_2$, 0.62 mM $MgCl_2$, 20 mM glucose, 20 mM HEPES, pH 7.4). The cells are then washed with assay buffer (i.e. HBS). The microtiter dish is then placed into a fluorescence plate reader (e.g., Fluoroskan II, Lab Products International., Ltd., Raleigh, N.C.), and the basal fluorescence of each well measured and recorded before addition of metabotropic receptor-modulating compounds such as quisqualate, glutamate, L-AP4, trans-ACPD (i.e., 1-amino-cyclopentane-1,3-dicarboxylic acid), 1S,3R-ACPD, AP3 (i.e., 2-amino-3-phosphonopropionate) AP5 (i.e., 2-amino-5-phosphonopentanoate), and CNQX (i.e., 6-cyano-7-nitroquinoxaline-2,3-dione) to the wells. The fluorescence of the wells is monitored repeatedly (75 readings at 0.63-sec intervals) following addition of agonist.

In general, the fluorescence of the untransfected host cells is not expected to change after addition of any of these compounds. The fluorescence of host cells transfected with the mGluR construct is expected to increase (if the mGluR being expressed is coupled to the PI hydrolysis pathway) or decrease (if the mGluR being expressed is coupled to inhibition of cyclic nucleotide generation or directly coupled to voltage-gated calcium channels) in response to application of agonist. In assays of mGluR that cause a decrease in cyclic nucleotide levels upon activation, it may be desirable to expose the cells (which also express cyclic nucleotide-gated channels) to forskolin and IBMX to elevate cyclic nucleotide levels and thereby enhance the detection of the signal resulting from the mGluR-induced decrease in cyclic nucleotide levels.

Dose-response studies in which the peak fluorescence values measured after application of varying amounts of mGluR agonists to cells transfected with mGluR-encoding DNA are compared, are expected to reveal that the magnitude of the peak fluorescence after addition of agonist changes with increasing concentration of each compound. Analysis of these data enables a calculation of $EC_{50}$ values for each compound used in determining the relative potencies of the compounds.

Mammalian host cells co-transfected with mGluR-encoding DNA linked to the MMTV inducible promoter and pRShGR (a glucocorticoid receptor construct) can also be analyzed in the fluorescence assay. The fluorescence of these cells changes in response to mGluR agonists; the peak response is greater when the cells are preincubated with dexamethasone (~1 $\mu$M) for 16 hrs at 37° C. before being assayed.

b. Fluorescence imaging assay

Mammalian host cells that have been transfected with mGluR-encoding DNA and untransfected host cells (control) are analyzed by digital video imaging in order to visualize metabotropic receptor-mediated changes in intracellular $Ca^{++}$ concentration. Transfectants ($4 \times 10^5$ cells per 35-mm culture dish with glass-insert bottom) are loaded with fura-2 by exposing the cells to 1 $\mu$M fura-2 (acetoxymethyl ester) for 25 min at room temperature in the dark. The cells are then washed three times with DMEM and four times with Ringer's (160 mM NaCl, 5 mM KCl, 2 mM $CaCl_2$, 1 mM $MgCl_2$, 11 mM glucose, 5 mM HEPES, pH 7.3) solution.

The transfectants and untransfected cells are then placed on the stage of an Axiovert 100 TV inverted microscope (Zeiss, Oberkochren, Germany), quipped with a 150 W xenon lamp as the UV light source. An Image 1 Fluor System (Universal Imaging, West Chester, Pa.) is used to control the alternate excitation of the cells at 350 and 380 nm (typically every 3 sec) through a 40× 1.3 N.A. oil immersion objective. Light emitted at greater than 510 nm is collected by a CCD 72 intensified CCD camera (MTI Dage, Michigan City, Ind.) and digitized. The background emitted light is subtracted from the 350 and 380 nm excitation images. The corrected values are used in calculating the 350/380 intensity ratio. These uncalibrated fura-2 ratio values are reliable indicators of changes in the intracellular $Ca^{++}$ concentration.

The uncalibrated fura-2 ratios are used to generate pseudocolor images with purple corresponding to resting intracellular $Ca^{++}$ concentration (~100 nM) and red to high intracellular $Ca^{++}$ concentration (~1 $\mu$M). For quantitative analysis, the average ratio value in a 12-by-12 pixel region over each cell is calculated by the software for each ratio image in an experiment and imported into a spreadsheet for further analysis and graphing.

To demonstrate that HEK 293 cells express the intracellular components required in receptor-mediated activation of the PI hydrolysis/$Ca^{++}$ mobilization pathway, transfectants and untransfected cells (which express endogenous G-protein-coupled muscarinic acetylcholine receptors) are exposed to 1 mM carbamylcholine (CCh; a muscarinic acetylcholine receptor agonist), and the cells are monitored for increases in intracellular $Ca^{++}$ concentration. Typically, a detectable increase in the intracellular $Ca^{++}$ concentration of the majority of the cells is observed in response to CCh addition in the imaging studies.

Both mGluR- transfected and untransfected HEK 293 cells are also monitored for changes in intracellular $Ca^{++}$ concentration in response to mGluR agonists. On average, the intracellular $Ca^{++}$ concentration of the untransfected cells is not expected to change after exposure to agonist. In contrast, the intracellular $Ca^{++}$ concentration of a significant percentage of the transfected cells is expected to change in response to application of agonist.

2. Phosphatidylinositol hydrolyis (IP$_1$) assays

Because activation of G-protein-coupled metabotropic receptors by agonists can lead to stimulation of the phosphatidylinositol (PI) hydrolysis pathway, methods of detecting increases in the products of PI hydrolysis (e.g., IP$_3$, IP$_2$ or IP$_1$) can be applied to the analysis of functional expression of metabotropic receptors that are coupled to the PI hydrolysis/Ca$^{++}$ mobilization pathway or to both the PI hydrolysis/Ca$^{++}$ mobilization pathway and the inhibitory cAMP cascade. One method for measuring IP$_1$ and/or IP$_2$ and/or IP$_3$ generated by hydrolysis of PI involves incorporation of [$^3$H]-myo-inositol into cell membrane phospholipids and subsequent separation of [$^3$H]-IP$_1$, [$^3$H]-IP$_2$ and [$^3$H]-IP$_3$, followed by quantitation of the radioactivity in each fraction, as follows Mammalian cells that have been transiently transfected with DNA encoding an mGluR that couples to the PI hydrolysis pathway are plated in 24-well microtiter plates at a density of 8×10$^5$ cells/well. After the cells are allowed to settle and adhere to the bottom of the plate for a few hours, 2 $\mu$Ci of [$^3$H]-myo-inositol (Amersham catalog #PT6–271, Arlington Heights, Ill.; specific activity=17.7 Ci/mmol) is added to each well and incubated overnight at 37° C. The next day, the cells are examined under a Nikon Diaphot inverted microscope to assess the health of the cells morphologically as well as to determine if the wells contained a confluent layer of cells. Media is then aspirated and the cells are washed twice with 0.5 ml Krebs bicarbonate buffer [117.9 mM NaCl, 4.72 mM KCl, 2.54 mM CaCl$_2$, 1.18 mM MgSO$_4$, 1.19 mM KH$_2$PO$_4$, 25 mM NaHCO$_3$, 1.11 mM dextrose (equilibrated with 95% O$_2$, 5% CO$_2$, pH 7.4)]. The cells are incubated for 45 min. at room temperature. The buffer is then aspirated from each well and the cells are washed and incubated in 0.5 ml/well for 45 min at room temperature. The buffer is aspirated from each well, and the cells are then incubated for 20 min at 37° C. with 450 $\mu$l Krebs-bicarbonate buffer containing 10 mM LiCl instead of 10 mM NaCl (to block hydrolysis of IP$_1$ to inositol and inorganic phosphate) and 10 mM unlabeled myoinositol.

To begin treatment of the cells with metabotropic receptor-modulating compounds, 50 $\mu$l of Krebs-bicarbonate buffer (control) or 10× the final concentration of the compound is added to each well and the incubation is continued for 40 min. Incubation is terminated by addition of 1 ml ice-cold methanol to each well.

In order to isolate IP$_1$ from the cells, the cells are removed from the plates by scraping with plastic pipette tips, and the cell suspension is transferred to 12×75 mm glass tubes. The tubes are thoroughly vortexed, and a 150-$\mu$l aliquot, i.e., one-tenth of the total volume, of each reaction mixture is transferred to another tube for protein determination. The water-soluble inositol phosphates are separated from the radiolabelled membrane phospholipids by extraction in 1 ml chloroform. The tubes are incubated at room temperature for 30 min before centrifugation at 500×g for 5 min at 4° C. The aqueous (top) layer containing the [$^{33}$H]-inositol phosphates is transferred to 10-ml syringes connected to Accell QMA SEP-PAK columns (Millipore; Calif.), which are attached to an Amersham Superseparator apparatus that is modified to allow collection into 20-ml scintillation vials. Water (10 ml) is added to the cartridge to remove [$^3$H]-inositol precursor, followed by 4 ml 0.02M triethylammonium hydrogen carbonated buffer (TEAB, Fluka; N.Y.). To separately remove [$^3$H]-IP$_1$, [$^3$H]-IP$_2$ and [$^3$H]-IP$_3$ from the cartridge, 4 ml of 0.1M TEAB, 4 ml of 0.3M TEAB and 4 ml of 0.4M TEAB are sequentially added to the cartridge and the separate eluate fractions are collected in large scintillation vials. Ecolume cocktail (15 ml; ICN; California) is added to each vial for subsequent scintillation counting to determine the amount of each IP in the separate fractions. Protein concentration is determined using the Bio-Rad Protein Micro-Assay (Bio-Rad, Richmond, Calif.).

To keep the basal levels of IP$_1$ low in cells expressing mGluRs, it may be beneficial to decrease the amount of mGluR-encoding DNA used for transfecting the cells, e.g., 0.18$\mu$g instead of 18 $\mu$g Lower basal levels enhance the dectectability of IP$_1$ concentration increases in mGluR-expressing cells treated with an mGluR agonist.

Dose-response studies which compare the IP$_1$ levels measured after application of varying amounts of mGluR agonist to cells transfected with mGluR-encoding DNA reveal that IP$_1$ levels increase with increasing concentration of agonist if the mGluR being expressed is coupled to the PI hydrolysis pathway. Analysis of these data enables calculation of EC$_{50}$ values for each compound which is used in determining the relative potencies of the compounds.

3. Metabotropic Receptor Ligand Binding Assays

Mammalian cells transfected with mGluR-encoding DNA or with pUC19 (negative control) are analyzed for [$^3$H]-glutamate binding. Rat brain membranes are included in the binding assays as a positive control.

a. Preparation of Membranes i. Rat forebrain membranes

Rat forebrain membranes are prepared from rat brains as described by Schoepp et al. [(1992) *Neurosci. Lett.* 145:100]. Briefly, forebrains, consisting essentially of cerebral cortex, striatum and hippocampus, from ten rat brains are homogenized in 50 volumes of 30 mM ice-cold Tris-HCl containing 2.5 mM CaCl$_2$, pH 7.6 using a Polytron (Brinkman, Westbury, N.Y.). The homogenate is centrifuged at 30,000×g for 15 minutes at 4° C. The supernatant is discarded, the pellet resuspended in 50 volumes of buffer using a Polytron and the suspension is centrifuged at 30,000×g for 15 min. This step is repeated twice. The pellet is resuspended in buffer and incubated at 37° C. for 30 min. The suspension is then centrifuged at 30,000×g for 15 min. at 4° C. This step is repeated three times. The final pellet is resuspended in 15 volumes of 50 mM Tris-HCl, pH 7.6, buffer, aliquoted, quick frozen and stored at −70° C.

ii. Membranes from Transfected and Untransfected Mammalian Cells

In order to prepare membranes from mammalian cells transfected with mGluR-encoding DNA or pUC19 (negative control) cells are scraped from the tissue culture plates, and the plates rinsed with 5 ml of PBS (phosphate-buffered saline: 137 mM NaCl, 2.7 mM KCl, 10 mM Na$_2$HPO$_4$, 1.7 mM KH$_2$PO$_4$). The cells are centrifuged at low speed in a table-top centrifuge, and the cell pellet is rinsed with PBS. The cell pellet is resuspended in 20 volumes of 50 mM Tris-HCl containing 0.5 mM PMSF, pH 7.6. The cells are homogenized on ice in a Dounce (teflon/glass) homogenizer using 10–20 strokes. The homogenate is centrifuged at 120,000×g for 30 min. at 4° C. The final membrane pellet is resuspended in 50 mM Tris-HCl containing 0.5 mM PMSF, pH 7.6. The membrane preparations are aliquoted, quick-frozen, and stored at −70° C. The protein concentration is determined using the method of Bradford [(1976) *Anal. Biochem.* 72:248].

b. [$^3$H]-Glutamate binding assays

Specific binding of [$^3$H]-glutamate to metabotropic receptors in rat forebrain membranes is determined basically as described by Schoepp et al. (supra). On the day of the assay, frozen homogenate is thawed and washed three times with 50 mM Tris-HCl, pH 7.6. The final pellet is resuspended in 50 mM Tris-HCl, pH 7.6. The protein concentration is determined using the method of Bradford [(1976) *Anal. Biochem.* 72:248]. The suspension is centrifuged at 30,000×g for 15 min. in order to be able to resuspend the pellet in the assay buffer (50 mM Tris-HCl, 0.5 mM PMSF, 0.1% BSA, pH 7.6) at a concentration of 1 mg/ml. The membrane suspension is incubated in triplicate with 10 or 100 nM [$^3$H]-glutamate (New England Nuclear, Boston, Mass.; catalog no. NET-490, specific activity=57.4 Ci/mmol) in a total volume of 0.5 ml assay buffer containing 100 μM NMDA (Sigma, St. Louis, Mo.), 100 μM AMPA and 100 μM kainate (Research Biochemicals Inc., Natick, Mass.) to block [$^3$H]-glutamate binding to ionotropic glutamate receptors and 100 μM SITS (Sigma, St. Louis, Mo.) to inhibit [$^3$H]-glutamate binding to chloride-dependent uptake sites for 45 min on ice. Bound radioactivity is separated from free radioactivity by centrifugation for 5 min. at 20,000×g (4° C.) in an SM-24 rotor (Sorvall, Wilmington, Del.). The pellets are washed twice with 5–6 ml of ice-cold 50 mM Tris-HCl buffer, pH 7.6. The pellets are solubilized by vortexing in 5 ml of Ecolume scintillation cocktail. The radioactivity is measured in a Beckman scintillation counter. The nonspecific binding observed in the presence of 1 mM glutamate is subtracted from the total binding in order to determine specific binding.

Specific binding of [$^3$H]-glutamate to membranes prepared from mammalian cells transfected with mGluR-encoding DNA or pUC19 is determined essentially as described for measuring binding to rat brain membranes with minor modifications. On the day of the assay, frozen homogenate is thawed and centrifuged in a MR-150 high-speed refrigerated microcentrifuge (Peninsula Laboratories, Inc., Belmont, Calif.). The pellet is washed twice with assay buffer (50 mM Tris-HCl, 0.5 mM PMSF, 0.1% BSA, pH 7.6), and the final pellet resuspended in assay buffer at a concentration of 1 mg/ml. NMDA, AMPA and kainate are excluded from the assay mixture when mammalian cell membranes are being analyzed for [$^3$H]-glutamate binding.

Specific binding of [$^3$H]-glutamate to rat brain membranes is measured using 200 μg of membrane and 100 nM [$^3$H]-glutamate. The ratio of total-to-nonspecific binding is typically approximately 2:1.

Specific binding of [$^3$H]-glutamate to membranes prepared from mammalian cells transfected with mGluR or pUC19 is measured using 200 μg of membranes and 100 nM [$^3$H]-glutamate. The amount of specific binding to membranes prepared from mammalian cells transfected with mGluR-encoding DNA is expected to be significantly higher than that to membranes prepared from mammalian cells transfected with pUC19. Competitive binding studies can be conducted in which the amount of specific binding of [$^3$H]-glutamate to membranes prepared from mammalian cells transfected with mGluR-encoding DNA in the presence of various concentrations of unlabeled glutamate is determined. IC$_{50}$ values are calculated from the data obtained in these studies.

The binding assays can also be performed using [$^3$H]-L-AP4 (Tocris Neuramin, Bristol, U.K.) in place of [$^3$H]-glutamate, and unlabelled L-AP4 to measure non-specific binding. The results of L-AP4 binding assays will reveal whether the mGluR being expressed in the host cell is a subtype that has affinity for L-AP4.

4. Cyclic AMP (cAMP) Assays a. RIA-based assays

Because activation of some G-protein-coupled receptors results in decreases (as opposed to increases) in cAMP, assays that measure intracellular cAMP levels can also be used to evaluate recombinant human metabotropic receptors expressed in mammalian host cells. Mammalian cells transiently or stably transfected with human metabotropic receptor-encoding DNA or pUC19 (negative control) are plated in 24-well microtiter plates at a density of 5×10$^5$ cells/well and allowed to incubate overnight. The following day, cells are examined under a Nikon Diaphot inverted microscope to assess the health of the cells morphologically as well as to determine if the wells contain a confluent layer of cells. Media is then aspirated and the cells are washed twice with 0.5 ml Krebs bicarbonate buffer (same buffer used in the PI hydrolysis assay; see Example 3.C.2) containing 1 mM IBMX (3-isobutyl-1-methylxanthine; Sigma, St. Louis, Mo.) and 0.1% BSA. Alternatively, 1× PBS can be used in place of Krebs bicarbonate buffer. Each wash is followed with a 30-min incubation at 37° C. The buffer is aspirated from each well and the cells are then incubated for 20 min at 37° C. with 0.2 ml Krebs-bicarbonate buffer containing 1 mM IBMX and 0.1% BSA.

To begin treatment of the cells with metabotropic receptor-modulating compounds, 50 μl of Krebs-bicarbonate buffer, with or without 5× the final concentration of forskolin, is added to some of the cells (basal control) and 5× the final concentration of the compound plus 5× the final concentration of forskolin is added to some cells (test cells) and the incubation is continued for 15 min at 37° C. At the end of this 15-min period, the reaction is terminated by adding 25 μl of 1% Triton X-100 solution and the incubation is continued for another 10 min. The lysed cells plus the cell suspension are transferred to 12×75 mm polypropylene tubes with plastic pipette tips. Each well is rinsed with 75 μl of Krebs-bicarbonate buffer containing 1 mM IBMX and 0.1% BSA. The rinse is combined with the cell lysate. The cell lysate suspension is centrifuged at 2300×g for 5 min and the supernatant is assayed for cAMP levels using an RIA kit (Amersham Life Sciences catalog #TRK 432; Arlington Heights, Ill.).

b. Cyclic nucleotide-gated channel-based assay i. Evaluation of Host. Cells Expressing Cyclic Nucleotide-Gated Channels Mammalian host cells, e.g., HEK293 cells, are grown in monolayers (approximately 2×10$^6$ cells per 10 cm poly-D-lysine-coated plate) in Dulbecco's modified Eagle's medium (DMEM; Gibco) containing 5% defined supplemented calf serum (Hyclone) including 100 U/ml penicillin and 100 μg/ml streptomycin sulfate. The cells are transiently transfected by the calcium phosphate method (see Ausubel, et al., supra, pp 9.1.1–9.1.7) with 5 μg of pCNV-OCNA (containing DNA encoding the olfactory cyclic nucleotide-gated channel (see Dhallan et al., supra) linked to the CHV promoter, 2 μg pCMV-βgal (Clontech, Palo Alto, Calif.), and 13 μg pUC19 as a control plasmid. The cells may optionally be co-transfected with DNA encoding a second subunit of the olfactory cyclic nucleotide-gated channel (i.e., rOCNC2; see Liman et al., *Neuron* 13:611–621 (1994) and Bradley et al., *Proc. Natl. Acad. Sci. USA* 91:8890–8894 (1994)).

Vector PCMV-OCNA is constructed by isolating the olfactory cyclic nucleotide-gated channel-encoding DNA as ~3.0 kb EcoRI fragment from pBluescript KS and ligating the resulting fragment to EcoRI-digested pCMV-T7-3. Plasmid pCMV-T7-3 is essentially identical to pCMV-T7-3(-SD/SA) (see Example 1) except that it contains SV40 splice donor/splice acceptor sites positioned between the CMV promoter and the T7 promoter/enhancer.

Six hours after transfection, the calcium phosphate precipitate is washed off and cells fed with DMEM containing 10% dialyzed fetal bovine serum (Hyclone), 100 U/ml penicillin, 100 μg/ml streptomycin, and supplemented with 2 mM glutamine. Transfection efficiencies, as determined by measuring β-galactosidase activity, are typically 50–70%.

HEK cells transfected with olfactory cyclic nucleotide-gated channel DNA are incubated 24–48 hours before testing for function. The activity of the channels is first assessed electrophysiologically using inside-out membrane patches pulled from the transfected cells so that the concentration of cAMP reaching the cytoplasmic face could be controlled (see, e.g., *Single-Channel Recording*, Sakmann and Neher, eds., Plenum Press, N.Y. (1983)). The patch is exposed to $Ca^{++}/Mg^{++}$-free Ringer's solution on both surfaces. In one patch, a current is elicited by ramping the membrane potential from −100 to +100 mV in 2 seconds, in the presence of 1 mM cAMP. This result suggests that the channel was functionally expressed.

The transfectants are also analyzed by single-cell video imaging of internal calcium levels ($[Ca^{++}]_i$). This method allows analysis of cyclic nucleotide-gated channel activity by measurement of intracellular calcium levels, which change with the amount of calcium influx through the channel, as regulated by cyclic nucleotide activation of the channel. The imaging assay is conducted essentially as described in Example 3.C.1.b. Software controls the alternate excitation of the cells at 350 and 385 nm (typically every 5 seconds) through a 40×1.3 N.A. oil immersion objective. Light emitted at greater than 510 nm is collected by the CCD camera, digitized, and 350 and 385 nm excitation images are background-subtracted before calculating the 350/385 nm intensity ratio.

For quantitative analysis, the average 350/385 ratio value in a 12 by 12 pixel region over each cell is calculated by the software for each ratio image in an experiment and imported into a spreadsheet for further analysis and graphing. Fura-2 signals are calibrated with an intact cell in which $R_{min}$ is obtained by exposing the cells to Ringer's solution containing 10 μM ionomycin, 10 mM EGTA and no added $Ca^{++}$. $R_{max}$ is next obtained by exposing the cells to Ringer's solution containing 10 μM ionomycin and 10 mM $Ca^{++}$, with three washes. Using a $K_d$ of 250 nM for fura-2 inside living cells and the equation of Grynkiewicz et al. (*J. Biol. Chem.* 260:3440 (1985)), the resting $[Ca^{++}]_i$ is typically 100 nM.

In these experiments the HEK293 cell transfectants are exposed to agents which increase intracellular cAMP levels and monitored for subsequent changes in $[Ca^{++}]_i$. There is typically a small increase in $[Ca^{++}]_i$ in the averaged results from 64 cells, and in individual cells in response to addition of 100 μM forskolin (activator of adenyl cyclase). A more significant increase is typically observed after addition of 1 mM IBMX (inhibitor of cAMP phosphodiesterase). Few if any, untransfected HEK 293 cells show an increase in $[Ca^{2+}]_i$ in response to elevation of intracellular cAMP levels. Any such response is transient and clearly different from the sustained response seen in HEK293 cells transfected with the cyclic nucleotide-gated channel DNA.

These results demonstrate that HEK cells expressing cyclic nucleotide-gated channels may be used as host cells in assays of receptors that cause a change in intracellular cyclic nucleotide levels when activated (e.g., metabotropic receptors).

ii. Co-Expression of Metabotropic Glutamate Receptors and Cyclic Nucleotide-Gated Channels Mammalian cells transfected with DNA encoding cyclic nucleotide-gated channels (e.g., pCMV-OCNA) can be simultaneously or successively co-transfected with DNA encoding human mGluRs as described in Example 3A and 3B. If the mGluR expressed in the cells is one that causes a decrease in cyclic nucleotide levels upon activation, then functional expression of the recombinant mGluR can be evaluated by analyzing the cells for decreases in intracellular $Ca^{2+}$ levels (due to decreased cyclic nucleotide-induced activation and resulting influx of $Ca^{+2}$ through cyclic nucleotide-gated channels) upon activation of the mGluRs.

Transfectants can be analyzed using single-cell video imaging as described in Example 3.C.4.b. (i). Application of 100 μM forskolin and 1 mM IBMX results in an increase in the fluorescence of the cells resulting from increases in intracellular calcium levels upon opening of the cyclic nucleotide-gated channel The forskolin/IBMX-induced fluorescence increase is detectably reduced in transfectants treated with mGluR agonist (preferably by a 2-min preincubation with agonist prior to applying forskolin/IBMX).

5. Northern Blot Hybridization Analysis

Cells transfected with human metabotropic receptor-encoding DNA can also be analyzed for expression of the corresponding transcript by northern blot analysis. Total RNA is isolated from ~1×10⁷ cells that have been transfected with the human metabotropic receptor-encoding DNA, and 10–15 μg of RNA is used for northern hybridization analysis The inserts from human metabotropic receptor-encoding plasmids are nick-translated and used as probes. Typical conditions for northern blot hybridization and washing are as follows:

hybridization in 5× SSPE, 5× Denhart's solution, 50% formamide, at 42° C. followed by washing in 0.2× SSPE, 0.1% SDS, at 65° C.

While the invention has been described in detail with reference to certain preferred embodiments thereof it will be understood that modifications and variations are within the spirit and scope of that which is described and claimed.

That which is claimed is:

1. An isolated polynucleotide encoding human metabotropic glutamate receptor subtype mGluR6.

2. A polynucleotide according to claim 1 wherein said polynucleotide encodes the amino acid sequence set forth in SEQ ID NO:2.

3. A polynucleotide according to claim 1 wherein said polynucleotide hybridizes under high stringency conditions to the coding region of SEQ ID NO:1.

4. A polynucleotide according to claim 1 wherein the nucleotide sequence of said polynucleotide is the same as the coding region (nucleotides 85–2718) of SEQ ID NO:1.

5. A polynucleotide according to claim 1 wherein said polynucleotide contains the 67 nucleotide sequence set forth in SEQ ID NO:3.

6. Nucleic acid probes comprising more than 46 contiguous bases of the polynucleotide according to claim 1 or the full complement thereof, wherein the probes specifically hybridize under stringent hybridization conditions to human mGluR6 encoding nucleic acid.

7. Nucleic acid probes comprising more than 46 contiguous bases of the polynucleotide according to claim 5 or the full complement thereof, wherein the probes specifically hybridize under stringent hybridization conditions to human mGluR6 encoding nucleic acid.

8. An isolated eukaryotic cell containing a polynucleotide according to claim 1.

9. An isolated eukaryotic cell expressing a polynucleotide of claim 1.

10. Amphibian oocytes expressing the polynucleotide of claim 1.

11. A method for identifying DNA encoding human metabotropic glutamate receptor protein subtype mGluR6, said method comprising:

contacting human DNA with a probe according to claim 6 under high stringency hybridization conditions, and identifying DNA which specifically hybridizes to said probe.

12. A method for identifying DNA encoding human metabotropic glutamate receptor protein subtype mGluR6, said method comprising:

contacting human DNA with a probe according to claim 7 under high stringency hybridization conditions, and identifying DNA which specifically hybridizes to said probe.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2961 base pairs
      (B) TYPE: nucleic acid
      (C) STRANDEDNESS: both
      (D) TOPOLOGY: both (ii) MOLECULE TYPE: cDNA (ix) FEATURE:
    (A) NAME/KEY: CDS
    (B) LOCATION: 85..2718
    (D) OTHER INFORMATION: /product= "Human Metabotropic
        Glutamate Receptor Subtype mGluR6"

(xi) SEQUENCE DESCRIPTION: SEQ ID NO:1:

```
CGACTGAGGG TGTTGGCCTC GGCCGAATCT GTCACAGACT TGTCCTGAAC CGACAGCGGC         60

TGGCGCAGCC CGCTAGACGA GCCG ATG GCG CGG CCC CGG AGA GCC CGG GAG           111
                          Met Ala Arg Pro Arg Arg Ala Arg Glu
                           1               5

CCG CTG CTC GTG GCG CTG CTG CCG CTG GCG TGG CTG GCG CAG GCG GGC          159
Pro Leu Leu Val Ala Leu Leu Pro Leu Ala Trp Leu Ala Gln Ala Gly
 10              15                  20                  25

CTG GCG CGC GCG GCG GGC TCT GTG CGC CTG GCG GGC GGC CTG ACG CTG          207
Leu Ala Arg Ala Ala Gly Ser Val Arg Leu Ala Gly Gly Leu Thr Leu
                 30                  35                  40

GGC GGC CTG TTC CCG GTG CAC GCG CGG GGC GCG GCG GGC CGG GCG TGC          255
Gly Gly Leu Phe Pro Val His Ala Arg Gly Ala Ala Gly Arg Ala Cys
             45                  50                  55

GGG CCG CTG AAG AAG GAG CAG GGC GTG CAC CGG CTG GAG GCC ATG CTG          303
Gly Pro Leu Lys Lys Glu Gln Gly Val His Arg Leu Glu Ala Met Leu
         60                  65                  70

TAC GCG CTG GAC CGC GTC AAC GCC GAC CCC GAG CTG CTG CCC GGC GTG          351
Tyr Ala Leu Asp Arg Val Asn Ala Asp Pro Glu Leu Leu Pro Gly Val
     75                  80                  85

CGC CTG GGC GCG CGG CTG CTG GAC ACC TGC TCG CGG GAC ACC TAC GCG          399
Arg Leu Gly Ala Arg Leu Leu Asp Thr Cys Ser Arg Asp Thr Tyr Ala
 90                  95                 100                 105

CTG GAG CAG GCG CTG AGC TTC GTG CAG GCG CTG ATC CGC GGC CGC GGC          447
Leu Glu Gln Ala Leu Ser Phe Val Gln Ala Leu Ile Arg Gly Arg Gly
                110                 115                 120

GAC GGC GAC GAG GTG GGC GTG CGC TGC CCG GGA GGC GTC CCT CCG CTG          495
Asp Gly Asp Glu Val Gly Val Arg Cys Pro Gly Gly Val Pro Pro Leu
            125                 130                 135

CGC CCC GCG CCC CCC GAG CGC GTC GTG GCC GTC GTG GGC GCC TCG GCC          543
Arg Pro Ala Pro Pro Glu Arg Val Val Ala Val Val Gly Ala Ser Ala
        140                 145                 150

AGC TCC GTC TCC ATC ATG GTC GCC AAC GTG CTG CGC CTG TTT GCG ATA          591
Ser Ser Val Ser Ile Met Val Ala Asn Val Leu Arg Leu Phe Ala Ile
    155                 160                 165

CCC CAG ATC AGC TAT GCC TCC ACA GCC CCG GAG CTC AGC GAC TCC ACA          639
Pro Gln Ile Ser Tyr Ala Ser Thr Ala Pro Glu Leu Ser Asp Ser Thr
170                 175                 180                 185

CGC TAT GAC TTC TTC TCC CGG GTG GTG CCA CCC GAC TCC TAC CAG GCG          687
Arg Tyr Asp Phe Phe Ser Arg Val Val Pro Pro Asp Ser Tyr Gln Ala
                190                 195                 200

CAG GCC ATG GTG GAC ATC GTG AGG GCA CTG GGA TGG AAC TAT GTG TCC          735
Gln Ala Met Val Asp Ile Val Arg Ala Leu Gly Trp Asn Tyr Val Ser
            205                 210                 215

ACG CTG GCC TCC GAG GGC AAC TAT GGC GAA AGT GGG GTT GAG GCC TTC          783
Thr Leu Ala Ser Glu Gly Asn Tyr Gly Glu Ser Gly Val Glu Ala Phe
        220                 225                 230

GTT CAG ATC TCC CGA GAG GCT GGG GGG GTC TGT ATT GCC CAG TCT ATC          831
Val Gln Ile Ser Arg Glu Ala Gly Gly Val Cys Ile Ala Gln Ser Ile
    235                 240                 245

AAG ATT CCC AGG GAA CCA AAG CCA GGA GAG TTC AGC AAG GTG ATC AGG          879
Lys Ile Pro Arg Glu Pro Lys Pro Gly Glu Phe Ser Lys Val Ile Arg
250                 255                 260                 265
```

-continued

| | |
|---|---|
| AGA CTC ATG GAG ACG CCC AAC GCC CGG GGC ATC ATC ATC TTT GCC AAT<br>Arg Leu Met Glu Thr Pro Asn Ala Arg Gly Ile Ile Ile Phe Ala Asn<br>                  270                      275                    280 | 927 |
| GAG GAT GAC ATC AGG CGG GTC CTG GAG GCA GCT CGC CAG GCC AAC CTG<br>Glu Asp Asp Ile Arg Arg Val Leu Glu Ala Ala Arg Gln Ala Asn Leu<br>                  285                      290                    295 | 975 |
| ACC GGC CAC TTC CTG TGG GTC GGC TCA GAC AGC TGG GGA GCC AAG ACC<br>Thr Gly His Phe Leu Trp Val Gly Ser Asp Ser Trp Gly Ala Lys Thr<br>                  300                      305                    310 | 1023 |
| TCA CCC ATC TTG AGC CTG GAG GAC GTG GCC GTT GGG GCC ATC ACC ATC<br>Ser Pro Ile Leu Ser Leu Glu Asp Val Ala Val Gly Ala Ile Thr Ile<br>                315                      320                    325 | 1071 |
| CTG CCC AAA AGG GCC TCC ATC GAC GGA TTT GAC CAG TAC TTC ATG ACT<br>Leu Pro Lys Arg Ala Ser Ile Asp Gly Phe Asp Gln Tyr Phe Met Thr<br>330                      335                      340                    345 | 1119 |
| CGA TCC CTG GAG AAC AAC CGC AGG AAC ATC TGG TTC GCC GAG TTC TGG<br>Arg Ser Leu Glu Asn Asn Arg Arg Asn Ile Trp Phe Ala Glu Phe Trp<br>                  350                      355                    360 | 1167 |
| GAA GAG AAT TTT AAC TGC AAA CTG ACC AGC TCA GGT ACC CAG TCA GAT<br>Glu Glu Asn Phe Asn Cys Lys Leu Thr Ser Ser Gly Thr Gln Ser Asp<br>                365                      370                    375 | 1215 |
| GAT TCC ACC CGC AAA TGC ACA GGC GAG GAA CGC ATC GGC CGG GAC TCC<br>Asp Ser Thr Arg Lys Cys Thr Gly Glu Glu Arg Ile Gly Arg Asp Ser<br>                380                      385                    390 | 1263 |
| ACC TAC GAG CAG GAG GGC AAG GTG CAG TTT GTG ATT GAT GCG GTG TAT<br>Thr Tyr Glu Gln Glu Gly Lys Val Gln Phe Val Ile Asp Ala Val Tyr<br>                395                      400                    405 | 1311 |
| GCC ATT GCC CAC GCC CTC CAC AGC ATG CAC CAG GCG CTC TGC CCT GGG<br>Ala Ile Ala His Ala Leu His Ser Met His Gln Ala Leu Cys Pro Gly<br>410                      415                      420                    425 | 1359 |
| CAC ACA GGC CTG TGC CCG GCG ATG GAA CCC ACC GAT GGG CGG ATG CTT<br>His Thr Gly Leu Cys Pro Ala Met Glu Pro Thr Asp Gly Arg Met Leu<br>                  430                      435                    440 | 1407 |
| CTG CAG TAC ATC CGA GCT GTC CGC TTC AAC GGC AGC GCA GGA ACC CCT<br>Leu Gln Tyr Ile Arg Ala Val Arg Phe Asn Gly Ser Ala Gly Thr Pro<br>                  445                      450                    455 | 1455 |
| GTG ATG TTC AAC GAG AAC GGC GAT GCG CCC GGG CGG TAC GAC ATC TTC<br>Val Met Phe Asn Glu Asn Gly Asp Ala Pro Gly Arg Tyr Asp Ile Phe<br>                460                      465                    470 | 1503 |
| CAG TAC CAG GCG ACC AAT GGC AGT GCC AGC AGT GGC GGG TAC CAG GCA<br>Gln Tyr Gln Ala Thr Asn Gly Ser Ala Ser Ser Gly Gly Tyr Gln Ala<br>                475                      480                    485 | 1551 |
| GTG GGC CAG TGG GCA GAG ACC CTC AGA CTG GAT GTG GAG GCC CTG CAG<br>Val Gly Gln Trp Ala Glu Thr Leu Arg Leu Asp Val Glu Ala Leu Gln<br>490                      495                      500                    505 | 1599 |
| TGG TCT GGC GAC CCC CAC GAG GTG CCC TCG TCT CTG TGC AGC CTG CCC<br>Trp Ser Gly Asp Pro His Glu Val Pro Ser Ser Leu Cys Ser Leu Pro<br>                  510                      515                    520 | 1647 |
| TGC GGG CCG GGG GAG CGG AAG AAG ATG GTG AAG GGC GTC CCC TGC TGT<br>Cys Gly Pro Gly Glu Arg Lys Lys Met Val Lys Gly Val Pro Cys Cys<br>                525                      530                    535 | 1695 |
| TGG CAC TGC GAG GCC TGT GAC GGG TAC CGC TTC CAG GTG GAC GAG TTC<br>Trp His Cys Glu Ala Cys Asp Gly Tyr Arg Phe Gln Val Asp Glu Phe<br>                540                      545                    550 | 1743 |
| ACA TGC GAG GCC TGT CCT GGG GAC ATG AGG CCC ACG CCC AAC CAC ACG<br>Thr Cys Glu Ala Cys Pro Gly Asp Met Arg Pro Thr Pro Asn His Thr<br>555                      560                      565 | 1791 |
| GGC TGC CGC CCC ACA CCT GTG GTG CGC CTG AGC TGG TCC TCC CCC TGG<br>Gly Cys Arg Pro Thr Pro Val Val Arg Leu Ser Trp Ser Ser Pro Trp<br>570                      575                      580                    585 | 1839 |

```
GCA GCC CCG CCG CTC CTC CTG GCC GTG CTG GGC ATC GTG GCC ACT ACC        1887
Ala Ala Pro Pro Leu Leu Leu Ala Val Leu Gly Ile Val Ala Thr Thr
            590                 595                 600

ACG GTG GTG GCC ACC TTC GTG CGG TAC AAC AAC ACG CCC ATC GTC CGG        1935
Thr Val Val Ala Thr Phe Val Arg Tyr Asn Asn Thr Pro Ile Val Arg
            605                 610                 615

GCC TCG GGC CGA GAG CTC AGC TAC GTC CTC CTC ACC GGC ATC TTC CTC        1983
Ala Ser Gly Arg Glu Leu Ser Tyr Val Leu Leu Thr Gly Ile Phe Leu
            620                 625                 630

ATC TAC GCC ATC ACC TTC CTC ATG GTG GCT GAG CCT GGG GCC GCG GTC        2031
Ile Tyr Ala Ile Thr Phe Leu Met Val Ala Glu Pro Gly Ala Ala Val
            635                 640                 645

TGT GCC GCC CGC AGG CTC TTC CTG GGC CTG GGC ACG ACC CTC AGC TAC        2079
Cys Ala Ala Arg Arg Leu Phe Leu Gly Leu Gly Thr Thr Leu Ser Tyr
650                 655                 660                 665

TCT GCC CTG CTC ACC AAG ACC AAC CGT ATC TAC CGC ATC TTT GAG CAG        2127
Ser Ala Leu Leu Thr Lys Thr Asn Arg Ile Tyr Arg Ile Phe Glu Gln
            670                 675                 680

GGC AAG CGC TCG GTC ACA CCC CCT CCC TTC ATC AGC CCC ACC TCA CAG        2175
Gly Lys Arg Ser Val Thr Pro Pro Pro Phe Ile Ser Pro Thr Ser Gln
            685                 690                 695

CTG GTC ATC ACC TTC AGC CTC ACC TCC CTG CAG GTG GTG GGG ATG ATA        2223
Leu Val Ile Thr Phe Ser Leu Thr Ser Leu Gln Val Val Gly Met Ile
            700                 705                 710

GCA TGG CTG GGG GCC CGG CCC CCA CAC AGC GTG ATT GAC TAT GAG GAA        2271
Ala Trp Leu Gly Ala Arg Pro Pro His Ser Val Ile Asp Tyr Glu Glu
715                 720                 725

CAG CGG ACG GTG GAC CCC GAG CAG GCC AGA GGG GTG CTC AAG TGC GAC        2319
Gln Arg Thr Val Asp Pro Glu Gln Ala Arg Gly Val Leu Lys Cys Asp
730                 735                 740                 745

ATG TCG GAT CTG TCT CTC ATC GGC TGC CTG GGC TAC AGC CTC CTG CTC        2367
Met Ser Asp Leu Ser Leu Ile Gly Cys Leu Gly Tyr Ser Leu Leu Leu
            750                 755                 760

ATG GTC ACG TGC ACA GTG TAC GCC ATC AAG GCC CGT GGC GTG CCC GAG        2415
Met Val Thr Cys Thr Val Tyr Ala Ile Lys Ala Arg Gly Val Pro Glu
            765                 770                 775

ACC TTC AAC GAG GCC AAG CCC ATC GGC TTC ACC ATG TAC ACC ACC TGC        2463
Thr Phe Asn Glu Ala Lys Pro Ile Gly Phe Thr Met Tyr Thr Thr Cys
            780                 785                 790

ATC ATC TGG CTG GCA TTC GTG CCC ATC TTC TTT GGC ACT GCC CAG TCA        2511
Ile Ile Trp Leu Ala Phe Val Pro Ile Phe Phe Gly Thr Ala Gln Ser
795                 800                 805

GCT GAA AAG ATC TAC ATC CAG ACA ACC ACG CTA ACC GTG TCC TTG AGC        2559
Ala Glu Lys Ile Tyr Ile Gln Thr Thr Thr Leu Thr Val Ser Leu Ser
810                 815                 820                 825

CTG AGT GCC TCG GTG TCC CTC GGC ATG CTC TAC GTA CCC AAA ACC TAC        2607
Leu Ser Ala Ser Val Ser Leu Gly Met Leu Tyr Val Pro Lys Thr Tyr
            830                 835                 840

GTC ATC CTC TTC CAT CCA GAG CAG AAT GTG CAG AAG CGA AAG CGG AGC        2655
Val Ile Leu Phe His Pro Glu Gln Asn Val Gln Lys Arg Lys Arg Ser
            845                 850                 855

CTC AAG GCC ACC TCC ACG GTG GCA GCC CCA CCC AAG GGC GAG GAT GCA        2703
Leu Lys Ala Thr Ser Thr Val Ala Ala Pro Pro Lys Gly Glu Asp Ala
            860                 865                 870

GAG GCC CAC AAG TAGCAGGGCA GGTGGGAACG GGACTGCTTG CTGCCTCTCC            2755
Glu Ala His Lys
            875

TTTCTTCCTC TTGCCTCGAG GTGGAAGCTG TATAGAGCCC GGGTCCACGG TGAACAGTCA     2815

GTGGCAGGGA GTTTGCCAAG ACCATGCTCC GCGTCGGTGG GGCTGGCCTT GAGAAGGAAC     2875
```

```
TGGACCCAGC TCTACCCCGA TTCCAGCATG TGAGCTTCAT GCTTCCTCAC CACAGACCAG    2935

ACTCGCTTCC CATGGTGGGA AACACC                                        2961
```

(2) INFORMATION FOR SEQ ID NO:2:

(i) SEQUENCE CHARACTERISTICS:
        (A) LENGTH: 877 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Arg Pro Arg Arg Ala Arg Glu Pro Leu Leu Val Ala Leu Leu
 1               5                  10                  15

Pro Leu Ala Trp Leu Ala Gln Ala Gly Leu Ala Arg Ala Ala Gly Ser
             20                  25                  30

Val Arg Leu Ala Gly Gly Leu Thr Leu Gly Gly Leu Phe Pro Val His
         35                  40                  45

Ala Arg Gly Ala Ala Gly Arg Ala Cys Gly Pro Leu Lys Lys Glu Gln
     50                  55                  60

Gly Val His Arg Leu Glu Ala Met Leu Tyr Ala Leu Asp Arg Val Asn
 65                  70                  75                  80

Ala Asp Pro Glu Leu Leu Pro Gly Val Arg Leu Gly Ala Arg Leu Leu
                 85                  90                  95

Asp Thr Cys Ser Arg Asp Thr Tyr Ala Leu Glu Gln Ala Leu Ser Phe
            100                 105                 110

Val Gln Ala Leu Ile Arg Gly Arg Gly Asp Gly Asp Glu Val Gly Val
        115                 120                 125

Arg Cys Pro Gly Gly Val Pro Pro Leu Arg Pro Ala Pro Pro Glu Arg
    130                 135                 140

Val Val Ala Val Val Gly Ala Ser Ala Ser Ser Val Ser Ile Met Val
145                 150                 155                 160

Ala Asn Val Leu Arg Leu Phe Ala Ile Pro Gln Ile Ser Tyr Ala Ser
                165                 170                 175

Thr Ala Pro Glu Leu Ser Asp Ser Thr Arg Tyr Asp Phe Phe Ser Arg
            180                 185                 190

Val Val Pro Pro Asp Ser Tyr Gln Ala Gln Ala Met Val Asp Ile Val
        195                 200                 205

Arg Ala Leu Gly Trp Asn Tyr Val Ser Thr Leu Ala Ser Glu Gly Asn
    210                 215                 220

Tyr Gly Glu Ser Gly Val Glu Ala Phe Val Gln Ile Ser Arg Glu Ala
225                 230                 235                 240

Gly Gly Val Cys Ile Ala Gln Ser Ile Lys Ile Pro Arg Glu Pro Lys
                245                 250                 255

Pro Gly Glu Phe Ser Lys Val Ile Arg Arg Leu Met Glu Thr Pro Asn
            260                 265                 270

Ala Arg Gly Ile Ile Ile Phe Ala Asn Glu Asp Asp Ile Arg Arg Val
        275                 280                 285

Leu Glu Ala Ala Arg Gln Ala Asn Leu Thr Gly His Phe Leu Trp Val
    290                 295                 300

Gly Ser Asp Ser Trp Gly Ala Lys Thr Ser Pro Ile Leu Ser Leu Glu
305                 310                 315                 320

Asp Val Ala Val Gly Ala Ile Thr Ile Leu Pro Lys Arg Ala Ser Ile
                325                 330                 335
```

-continued

```
Asp Gly Phe Asp Gln Tyr Phe Met Thr Arg Ser Leu Glu Asn Asn Arg
        340                 345                 350

Arg Asn Ile Trp Phe Ala Glu Phe Trp Glu Asn Phe Asn Cys Lys
            355                 360                 365

Leu Thr Ser Ser Gly Thr Gln Ser Asp Asp Ser Thr Arg Lys Cys Thr
    370                 375                 380

Gly Glu Glu Arg Ile Gly Arg Asp Ser Thr Tyr Glu Gln Gly Lys
385                 390                 395                 400

Val Gln Phe Val Ile Asp Ala Val Tyr Ala Ile Ala His Ala Leu His
                405                 410                 415

Ser Met His Gln Ala Leu Cys Pro Gly His Thr Gly Leu Cys Pro Ala
            420                 425                 430

Met Glu Pro Thr Asp Gly Arg Met Leu Leu Gln Tyr Ile Arg Ala Val
            435                 440                 445

Arg Phe Asn Gly Ser Ala Gly Thr Pro Val Met Phe Asn Glu Asn Gly
450                 455                 460

Asp Ala Pro Gly Arg Tyr Asp Ile Phe Gln Tyr Gln Ala Thr Asn Gly
465                 470                 475                 480

Ser Ala Ser Ser Gly Tyr Gln Ala Val Gly Gln Trp Ala Glu Thr
                485                 490                 495

Leu Arg Leu Asp Val Glu Ala Leu Gln Trp Ser Gly Asp Pro His Glu
            500                 505                 510

Val Pro Ser Ser Leu Cys Ser Leu Pro Cys Gly Pro Gly Glu Arg Lys
        515                 520                 525

Lys Met Val Lys Gly Val Pro Cys Cys Trp His Cys Glu Ala Cys Asp
        530                 535                 540

Gly Tyr Arg Phe Gln Val Asp Glu Phe Thr Cys Glu Ala Cys Pro Gly
545                 550                 555                 560

Asp Met Arg Pro Thr Pro Asn His Thr Gly Cys Arg Pro Thr Pro Val
                565                 570                 575

Val Arg Leu Ser Trp Ser Ser Pro Trp Ala Ala Pro Pro Leu Leu Leu
            580                 585                 590

Ala Val Leu Gly Ile Val Ala Thr Thr Thr Val Val Ala Thr Phe Val
            595                 600                 605

Arg Tyr Asn Asn Thr Pro Ile Val Arg Ala Ser Gly Arg Glu Leu Ser
610                 615                 620

Tyr Val Leu Leu Thr Gly Ile Phe Leu Ile Tyr Ala Ile Thr Phe Leu
625                 630                 635                 640

Met Val Ala Glu Pro Gly Ala Ala Val Cys Ala Ala Arg Arg Leu Phe
                645                 650                 655

Leu Gly Leu Gly Thr Thr Leu Ser Tyr Ser Ala Leu Leu Thr Lys Thr
            660                 665                 670

Asn Arg Ile Tyr Arg Ile Phe Glu Gln Gly Lys Arg Ser Val Thr Pro
        675                 680                 685

Pro Pro Phe Ile Ser Pro Thr Ser Gln Leu Val Ile Thr Phe Ser Leu
    690                 695                 700

Thr Ser Leu Gln Val Val Gly Met Ile Ala Trp Leu Gly Ala Arg Pro
705                 710                 715                 720

Pro His Ser Val Ile Asp Tyr Glu Glu Gln Arg Thr Val Asp Pro Glu
                725                 730                 735

Gln Ala Arg Gly Val Leu Lys Cys Asp Met Ser Asp Leu Ser Leu Ile
            740                 745                 750

Gly Cys Leu Gly Tyr Ser Leu Leu Leu Met Val Thr Cys Thr Val Tyr
        755                 760                 765
```

```
Ala Ile Lys Ala Arg Gly Val Pro Glu Thr Phe Asn Glu Ala Lys Pro
    770             775                 780
Ile Gly Phe Thr Met Tyr Thr Thr Cys Ile Ile Trp Leu Ala Phe Val
785             790                 795                 800
Pro Ile Phe Phe Gly Thr Ala Gln Ser Ala Glu Lys Ile Tyr Ile Gln
                805             810                 815
Thr Thr Thr Leu Thr Val Ser Leu Ser Leu Ser Ala Ser Val Ser Leu
            820             825                 830
Gly Met Leu Tyr Val Pro Lys Thr Tyr Val Ile Leu Phe His Pro Glu
        835             840                 845
Gln Asn Val Gln Lys Arg Lys Arg Ser Leu Lys Ala Thr Ser Thr Val
    850             855                 860
Ala Ala Pro Pro Lys Gly Glu Asp Ala Glu Ala His Lys
865             870                 875

(2) INFORMATION FOR SEQ ID NO:3:

(i) SEQUENCE CHARACTERISTICS:
        (A) LENGTH: 67 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..66

(xi) SEQUENCE DESCRIPTION: SEQ ID NO:3:

CGG AGC ACG GCA CCC CAG GGA GGG AGC CGG GTG CAT TGC AGC AAT GGA         48
Arg Ser Thr Ala Pro Gln Gly Gly Ser Arg Val His Cys Ser Asn Gly
  1               5                  10                  15

GGG CCA GGA AAG GCA CCG T                                               67
Gly Pro Gly Lys Ala Pro
             20

(2) INFORMATION FOR SEQ ID NO:4:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:4:

Arg Ser Thr Ala Pro Gln Gly Gly Ser Arg Val His Cys Ser Asn Gly
  1               5                  10                  15

Gly Pro Gly Lys Ala Pro
             20
```